US009447428B2

(12) United States Patent
Brinker et al.

(10) Patent No.: US 9,447,428 B2
(45) Date of Patent: Sep. 20, 2016

(54) SOYBEAN TRANSGENIC EVENT MON 87708 AND METHODS OF USE THEREOF

(71) Applicant: Monsanto Technology LLC, St. Louis, MO (US)

(72) Inventors: Ronald J. Brinker, Ellisville, MO (US); Wen C. Burns, Chesterfield, MO (US); Paul C. C. Feng, Wildwood, MO (US); Anju Gupta, Ankeny, IA (US); Sio-Wai Hoi, St. Louis, MO (US); Marianne Malven, Ellisville, MO (US); Kunsheng Wu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 455 days.

(21) Appl. No.: 13/945,741

(22) Filed: Jul. 18, 2013

(65) Prior Publication Data
US 2014/0041075 A1  Feb. 6, 2014

Related U.S. Application Data

(62) Division of application No. 12/868,989, filed on Aug. 26, 2010, now Pat. No. 8,501,407.

(60) Provisional application No. 61/243,227, filed on Sep. 17, 2009.

(51) Int. Cl.
| *A01H 5/00* | (2006.01) |
| *A01H 5/10* | (2006.01) |
| *C12N 15/52* | (2006.01) |
| *C12N 15/82* | (2006.01) |
| *A23D 9/00* | (2006.01) |
| *A23L 1/20* | (2006.01) |
| *C12Q 1/68* | (2006.01) |

(52) U.S. Cl.
CPC ............ *C12N 15/8274* (2013.01); *A23D 9/00* (2013.01); *A23L 1/2003* (2013.01); *C12Q 1/6895* (2013.01)

(58) Field of Classification Search
None
See application file for complete search history.

(56) References Cited

U.S. PATENT DOCUMENTS

| 5,850,019 | A | 12/1998 | Maiti et al. |
| 5,914,451 | A | 6/1999 | Martinell et al. |
| 7,022,896 | B1 | 4/2006 | Weeks et al. |
| 7,241,567 | B2 | 7/2007 | Weyens et al. |
| 7,851,670 | B2 | 12/2010 | Wan et al. |
| 7,939,721 | B2 | 5/2011 | Arnevik et al. |
| 2003/0115626 | A1 | 6/2003 | Weeks et al. |
| 2004/0117870 | A1 | 6/2004 | Weyens et al. |
| 2008/0015110 | A1* | 1/2008 | Clemente ............. C12N 9/0069 504/324 |
| 2008/0119361 | A1 | 5/2008 | Feng et al. |
| 2008/0120739 | A1 | 5/2008 | Wan et al. |
| 2008/0166699 | A1 | 7/2008 | Baley et al. |
| 2008/0305952 | A1 | 12/2008 | Arnevik et al. |
| 2009/0081760 | A1 | 3/2009 | D'Ordine et al. |
| 2009/0199308 | A1 | 8/2009 | Duff et al. |
| 2011/0067134 | A1 | 3/2011 | Brinker et al. |
| 2011/0067141 | A1 | 3/2011 | Froman et al. |
| 2011/0302667 | A1 | 12/2011 | Brown et al. |
| 2014/0373190 | A1 | 12/2014 | Brown et al. |
| 2015/0119248 | A1 | 4/2015 | Brown et al. |

FOREIGN PATENT DOCUMENTS

| CL | 83-08 | 1/2008 |
| CN | 101460626 A | 6/2009 |
| CN | 101501196 A | 8/2009 |
| CN | 10636498 A | 1/2010 |
| UA | A200810227 | 12/2008 |
| WO | WO 98/45424 | 10/1998 |
| WO | WO 2005/061720 | 7/2005 |
| WO | WO/2007/143690 | 12/2007 |
| WO | WO 2007/146706 A2 | 12/2007 |
| WO | WO 2008/105890 | 9/2008 |
| WO | WO/2009/102873 | 8/2009 |

OTHER PUBLICATIONS

Hohe et al, Plant Cell Rep. (2003) 21:1135-1142.*
U.S. Appl. No. 14/179,524, filed Feb. 12, 2014, Froman et al.
English language translation of Chilean Application No. CL 83-08, filed Jan. 11, 2008.
U.S. Appl. No. 14/745,241, filed Jun. 19, 2015, Brinker et al.
Wang et al., "Characterization of Cellular and Enzymatic Degradation of Dicamba by Pseudomonas maltophilia, Strain DI-6," dissertation presented to the Faculty of the Graduate Collage at the University of Nebraska, 1996.
Behrens et al., "Dicamba resistance: enlarging and preserving Biotechnology-based weed management strategies," *Science*, 316:1185-1188, 2007.
Carter et al., "Evaluating weed control options in dicamba toelrant soybean," *North Central Weed Science Society Proc.*, Abstract and Poster, 63:25 2008.
Carter et al., "Resistant weed management using dicamba tolerant soybean," Weed Science Society of America Annual meeting, Orlando, FL, Feb. 9-13, 2009.

(Continued)

*Primary Examiner* — Mykola Kovalenko
(74) *Attorney, Agent, or Firm* — Dentons US LLP; Pamela Sisson

(57) ABSTRACT

The invention provides a transgenic soybean event MON 87708 plant and plants, plant cells, seeds, plant parts, and commodity products derived from event MON 87708. The invention also provides polynucleotides specific for event MON 87708 and plants, plant cells, seeds, plant parts, and commodity products comprising polynucleotides specific for event MON 87708. The invention also provides methods related to event MON 87708.

16 Claims, 1 Drawing Sheet

(56) References Cited

OTHER PUBLICATIONS

Carter et al., "Evaluation of dicamba tolerant soybean in Kentucky: a three-year review," Weed Science Society of America Annual Meeting, Denver, CO, Feb. 7-11, 2010.
CLARITY herbicide EPA Reg. No. 7969-137, BASF, For use on dicamba-tolerant soybean MON 87708—grown for research, field trials, and seed production only, accepted with comments in EPA letter dated Feb. 13, 2008, Supplemental Label.
CLARITY herbicide EPA Reg. No. 7969-137, BASF, For use on dicamba-tolerant soybean MON 87708—grown for seed production only, Feb. 26, 2009, Supplemental Label.
CLARITY herbicide, EPA Reg. No. 7969-137, BASF, For use on dicamba-tolerant soybean MON 87708—Grown for research, field trials, and see production only, including USDA regulated plantings or seed production, accepted with comments in EPA letter dated May 28, 2010, Supplemental Label.
GenBank Accession No. CW906303, dated Dec. 8, 2004.
GenBank Accession No. EI363554, dated Feb. 16, 2007.
Hayes et al., "Glyphosate resistant horseweed control in dicamba-glyphosate resistant soybeans," *Southern Weed Science Society Proceedings*, 61:51, 2008, Abstract
Rychik et al., "A computer program for choosing optimal oligonucleotides for filter hybridization, sequencing and in vitro amplification of DNA," *Nucleic Acids Res.*, 17(21):8543-51, 1989.
Steckel et al., "Glyphosate-resistant horseweed control in dicamba glyphosate resistant soybeans," *North Central Weed Science Society Proc.*, 63:92, 2008.
Steckel et al., "Glyphosate-resistant horseweed control in soybean tolerant to both dicamba and glyphosate," *North Central Weed Science Society Proceedings*, 62:178, 2007.
New England BioLabs Inc., 1998/99 Catalog, Nucleic Acids, Linkers and Primers, pp. 121 and 284.
Final Office Action regarding U.S. Appl. No. 11/801,114, dated Aug. 26, 2009.
International Preliminary Report on Patentability PCT/US2007/070517 (WO2007-143690), Dec. 10, 2008.
International Preliminary Report on Patentability PCT/US2009/033930 (WO2009-102873), Aug. 17, 2010.
International Preliminary Report on Patentability PCT/US2010/046759 (WO2011-034704), May 3, 2012.
U.S. Appl. No. 14/333,479, filed Jul. 16, 2014, Brown et al.
USPTO: Notice of Allowance for U.S. Appl. No. 13/151,082, issued Jun. 17, 2014.
NCBI GenBank Accession No. AC207600.4, "Medicago truncatula chromosome 2 BAC clone mth2-31i16, complete sequence," dated Oct. 27, 2007.
NCBI GenBank Accession No. ET721878.1, "CHO_OF124xh18fl.ab1 CHO_OF Nicotiana tabacum genomin 5-, genomic survey sequence," dated Jun. 20, 2008.
Gruzdev, "Chemical protection of plants," *Agropromizdat* (in Russian), 3rd edition, p. 316, 1987.
Prohorov et al., *Grand Soviet Encyclopedia* (in Russian), 16:233, 1974.
English translation of pp. 7-9 of Office Action issued in Russian Application No. 2012115127 dated Aug. 13, 2014.
Elke et al., "Analytical methods for detection and determination of genetically modified organisms in agricultural crops and plant-derived food products," *Eur Food Res Technol*, 214:3-26. 2001.
Sequence alignment information as indicated in transmittal letter of Nov. 25, 2013 Information Disclosure Statement for U.S. Appl. No. 13/945,741.
Astaurov et al., *Great Soviet Encyclopedia* (in Russian), article "Biology," 1970.
Berdal et al., "Roundup Ready® soybean even-specific real-time quantitative PCR assay and estimation of the practical detection and quantification limits in GMO analyses" *Eur Food Res Technol* 213:432-438, 2001.
Coruzzi et al., "Tissue-specific and light-regulated expression of a pea nuclear gene encoding the small subunit of ribulose-1,5-bisphospate carboxylase," *The EMBO Journal* 3(8):1671-1679, 1984.
English translation of p. 2 of Office Action issued in Ukrainian Application No. a201204680 , dated Jan. 26, 2015.
GenBank Accession No. AY786443, Dated Jun. 29, 2005.
Herman et al., "A Three-component Dicamba O-Demethylase from Pseudomonas maltohphilia, Strain DI-6," *The Journal of Biological Chemistry* 280(26):24759-24767, 2005.
Zimmermann et al., "Event Specific Transgene Detection in Bt11 Corn by Quantitative PCR at the Integration Site," *Lebensm.-Wiss. u.-Technol.*, 33(3):210-216, 2000.
English translation of Office Action regarding Japanese Patent Application No. 2014-235817, dated Dec. 8, 2016.
Yamauchi et al., Series "Food Science," *Soybean Science* 1(5):188-194, 1997.
Non-Final Office Action regarding U.S. Appl. No. 14/745,241, dated May 5, 2016.
Response to Non-Final Office Action regarding U.S. Appl. No. 14/745,241, dated Jun. 21, 2016.

\* cited by examiner

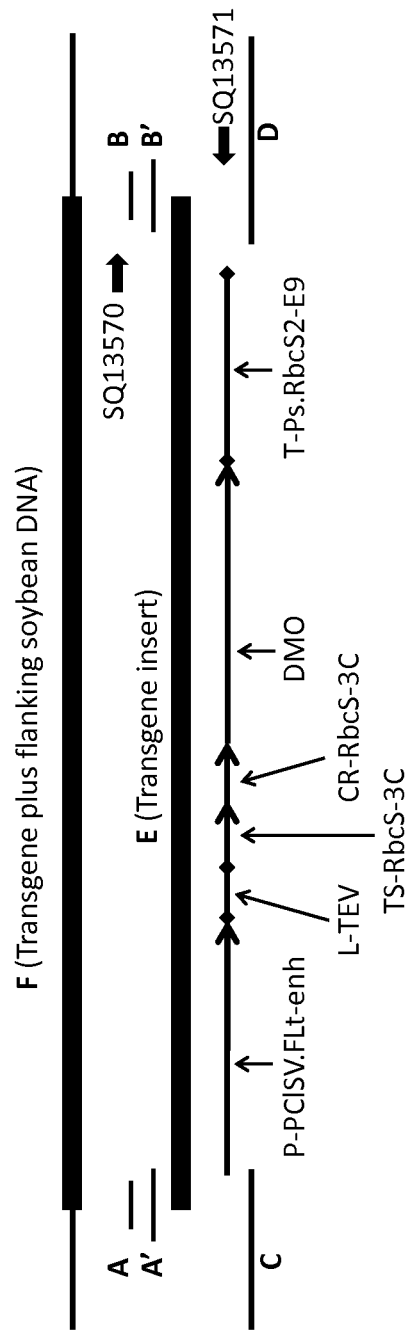

000
SOYBEAN TRANSGENIC EVENT MON 87708 AND METHODS OF USE THEREOF

CROSS REFERENCE TO RELATED APPLICATIONS

This application is a divisional of U.S. application Ser. No. 12/868,989, filed Aug. 26, 2010, which application claims the benefit of priority to U.S. Provisional Application No. 61/243,227, filed Sep. 17, 2009, which are herein incorporated by reference in their entireties.

INCORPORATION OF SEQUENCE LISTING

The sequence listing that is contained in the file named "55544-0001_seqlisting.txt", which is 19.5 kilobytes (size as measured in Microsoft Windows®) and was created on Aug. 13, 2010, is filed herewith by electronic submission and is incorporated by reference herein.

FIELD OF THE INVENTION

The invention relates to transgenic *Glycine max* event MON 87708. The event exhibits tolerance to dicamba herbicide. The invention also relates to plants, plant parts, plant seeds, plant cells, agricultural products, and methods related to event MON 87708 and provides nucleotide molecules that are unique to the event and were created in connection with the insertion of transgenic DNA into the genome of a *Glycine max* plant.

BACKGROUND OF THE INVENTION

Soybean (*Glycine max*) is an important crop in many areas of the world, and the methods of biotechnology have been applied to this crop in order to produce soybean with desirable traits. One such desirable trait is herbicide tolerance. The expression of an herbicide tolerance transgene in a plant can confer the desirable trait of herbicide tolerance on the plant, but expression of the transgene may be influenced by the chromosomal location and the genomic result of the transgene insertion. For example, it has been observed in plants that there often is variation in the level and pattern of transgene expression among individual events that differ in the chromosomal insertion site of the transgene but are otherwise identical. There may also be undesirable and/or desirable phenotypic or agronomic differences between events. Because of this, it is often necessary to produce and analyze a large number of individual plant transformation events in order to select an event having both the desirable trait and the optimal phenotypic and agricultural characteristics necessary to make it suitable for commercial purposes. Such selection often requires greenhouse and field trials with many events over multiple years, in multiple locations, and under a variety of conditions so that a significant amount of agronomic, phenotypic, and molecular data may be collected. The resulting data and observations must then be analyzed by teams of scientists and agronomists with the goal of selecting a commercially suitable event. Such an event, once selected, may then be used for introgressing the desirable trait into other genetic backgrounds using plant breeding methods, and thus producing a number of different crop varieties that contain the desirable trait and are suitably adapted to specific local growing conditions.

SUMMARY OF THE INVENTION

The invention provides transgenic soybean plants designated event MON 87708, which exhibit commercially acceptable tolerance to applications of dicamba herbicide, having representative seed deposited with American Type Culture Collection (ATCC) with Accession No. PTA-9670. The invention also provides novel DNA molecules related to soybean event MON 87708 and methods of using these molecules. The invention also provides seeds, progeny, plant parts, cells, and commodity products of soybean event MON 87708. The invention also provides methods of using soybean event MON 87708 and methods of producing dicamba tolerant soybean.

The invention provides recombinant DNA molecules related to soybean event MON 87708. These recombinant DNA molecules may comprise nucleotide molecules having a nucleotide sequence representing a region of the genomic DNA flanking the transgene insertion, and/or a region of the transgene insertion, and/or a contiguous sequence of any of these regions such as a region of the junction between the transgene insertion and flanking genomic DNA of soybean event MON 87708. The invention also provides DNA molecules useful as primers and probes diagnostic for soybean event MON 87708 and amplicons diagnostic for the presence of soybean event MON 87708. Soybean plants, plant cells, plant parts, commodity products, progeny, and seeds comprising these molecules are also disclosed.

The invention provides methods, compositions, and kits useful for detecting the presence and/or absence of DNA derived from soybean event MON 87708 and thus the presence and/or absence of the event. The invention provides a method for detection of MON 87708 by contacting a sample comprising DNA with a primer set that when used in a nucleic acid amplification reaction with genomic DNA from soybean event MON 87708 produces an amplified DNA diagnostic for soybean event MON 87708, performing a nucleic acid amplification reaction thereby producing the amplified DNA, and detecting the presence and/or absence of the amplified DNA. The invention also provides a method for detection of MON 87708 by contacting a sample comprising DNA with a probe that when used in a hybridization reaction with DNA from soybean event MON 87708 hybridizes to a DNA molecule specific for soybean event MON 87708, performing a hybridization reaction, and detecting the hybridization of the probe to the DNA molecule. Kits comprising the methods and compositions of the invention useful for detecting the presence of DNA derived from soybean event MON 87708 are also provided.

The invention provides a soybean plant, seed, plant cell, progeny plant, plant part, or commodity product derived from a plant, plant cell, or seed of soybean event MON 87708. The invention also provides a soybean plant, seed, plant cell, progeny plant, plant part, or commodity product comprising a recombinant DNA molecule having a nucleotide sequence selected from the group consisting of SEQ ID NO: 1-8, and complements and fragments thereof. The invention also provides a soybean plant, seed, plant cell, progeny plant, plant part, or commodity product derived from the plant or seed of soybean event MON 87708 and comprising a recombinant DNA molecule that produces an amplified DNA molecule comprising SEQ ID NO: 1, SEQ ID NO: 2, SEQ ID NO: 7, and/or SEQ ID NO: 8 in a DNA amplification method.

The invention provides a method for controlling weeds in a field by planting soybean event MON 87708 and then applying an effective dose of dicamba herbicide capable of controlling the weeds without injuring the soybean event MON 87708 plants. The invention also provides a method for controlling weeds in a field by applying an effective dose of dicamba herbicide to control weeds in a field and then planting soybean event MON 87708 in the field. The invention also provides a method for producing soybean seed essentially free of the seeds of toxic weed species by planting seeds of a dicamba tolerant soybean variety MON 87708 in a field, applying a post-emergence effective dose of dicamba herbicide sufficient to kill the toxic weed species to the field, and harvesting seed from the field.

The invention provides methods of producing a soybean plant and/or seed that tolerates application of dicamba herbicide by sexually crossing a soybean event MON 87708 plant comprising SEQ ID NO: 1, SEQ ID NO: 2, SEQ ID NO: 7, and/or SEQ ID NO: 8 with a second soybean plant, thereby producing seed, growing the seed to produce progeny plants, treating the progeny plants with dicamba, and selecting a progeny plant that is tolerant to dicamba. The methods may also include selfing the selected progeny plant to produce a plurality of second generation progeny plants and selecting from these a dicamba tolerant plant. The methods may also include sexually crossing the selected progeny plant with another soybean plant to produce seed, growing the seed to produce a second generation of progeny plants, treating the second generation of progeny plants with dicamba, and selecting a second generation progeny plant that is tolerant to dicamba. The invention provides methods of producing a soybean plant and/or seed that tolerates application of dicamba herbicide by selfing a dicamba tolerant soybean event MON 87708 plant comprising SEQ ID NO: 1, SEQ ID NO: 2, SEQ ID NO: 7, and/or SEQ ID NO: 8, thereby producing seed, growing the seed to produce progeny plants, treating the progeny plants with dicamba; and selecting a progeny plant that is tolerant to dicamba.

The invention provides methods of determining the zygosity of a soybean event MON 87708 plant or seed comprising contacting a soybean DNA sample with a primer set comprising SEQ ID NO: 12, SEQ ID NO: 13, and SEQ ID NO: 14 and a probe set comprising SEQ ID NO: 15 and SEQ ID NO: 16; then performing a nucleic acid amplification reaction with the sample, primer set, and probe set; then detecting in then nucleic acid amplification reaction a first fluorescent signal that is diagnostic for event MON 87708 and a second fluorescent signal different from the first fluorescent signal and that is diagnostic for native soybean genomic DNA corresponding to the location of insertion of the event MON 87708 transgene; and analyzing the presence and/or absence of the first fluorescent signal and the second fluorescent signal in the nucleic acid amplification reaction, wherein the presence of both fluorescent signals indicates the sample is heterozygous for event MON 87708 and the presence of only the first fluorescent signal indicates the sample is homozygous for event MON 87708.

The invention also provides a soybean plant, seed, plant cell, or plant part comprising soybean haplotype region on linkage group 9 at approximately map position 143.5 comprising a dicamba tolerance gene and further defined by haplotype window 19743 and 19767, and methods of using the same. The foregoing and other aspects of the invention will become more apparent from the following detailed description.

BRIEF DESCRIPTION OF THE DRAWINGS

FIG. 1 illustrates the organization of the transgenic insert in the genome of soybean event MON 87708; [A] corresponds to the relative position of SEQ ID NO: 1, which is sixty nucleotides of the junction between the soybean genomic DNA and the 5' portion of the transgene insert DNA; [A'] corresponds to the relative position of SEQ ID NO: 7, which is one hundred nucleotides of the junction between the soybean genomic DNA and the 5' portion of the transgene insert DNA; [B] corresponds to the relative position of SEQ ID NO: 2, which is sixty nucleotides of the junction between the soybean genomic DNA and the 3' portion of the transgene insert DNA; [B'] corresponds to the relative position of SEQ ID NO: 8, which is one hundred nucleotides of the junction between the soybean genomic DNA and the 3' portion of the transgene insert DNA; [C] corresponds to the relative position of SEQ ID NO: 3, which is the soybean genome sequence flanking the arbitrarily assigned/designated 5' end of the expression cassette integrated into the genome in event MON 87708; [D] corresponds to the relative position of SEQ ID NO: 4, which is the soybean genome sequence flanking the arbitrarily assigned/designated 3' end of the expression cassette integrated into the genome in event MON 87708; [E] represents the various elements comprising SEQ ID NO: 5 and is the sequence of the expression cassette inserted into the genome of the event MON 87708; and [F] represents the contiguous sequence (provided as SEQ ID NO: 6) comprising, as represented in the FIGURE from left to right, SEQ ID NO: 3, SEQ ID NO: 5 and SEQ ID NO: 4, in which SEQ ID NO: 1, SEQ ID NO: 2, SEQ ID NO: 7, and SEQ ID NO: 8 are included, as these sequences are present in the genome in event MON 87708.

BRIEF DESCRIPTION OF THE SEQUENCES

SEQ ID NO: 1 is a sixty nucleotide sequence representing the 5' junction between the soybean genomic DNA and the integrated transgenic expression cassette. SEQ ID NO: 1 is positioned in SEQ ID NO: 6 at nucleotide position 1097-1156.

SEQ ID NO: 2 is a sixty nucleotide sequence representing the 3' junction between the soybean genomic DNA and the integrated transgenic expression cassette. SEQ ID NO: 2 is positioned in SEQ ID NO: 6 at nucleotide position 4100-4159.

SEQ ID NO: 3 is the 5' sequence flanking the inserted DNA of soybean event MON 87708 up to and including a region of transgene DNA insertion.

SEQ ID NO: 4 is the 3' sequence flanking the inserted DNA of soybean event MON 87708 up to and including a region of transgene DNA insertion.

SEQ ID NO: 5 is the sequence of the integrated transgenic expression cassette.

SEQ ID NO: 6 is the nucleotide sequence representing the contig of the 5' sequence flanking the inserted DNA of soybean event MON 87708 (SEQ ID NO: 3), the sequence of the inserted DNA (SEQ ID NO: 5), and the 3' sequence flanking the inserted DNA of soybean event MON 87708 (SEQ ID NO: 4) and includes SEQ ID NO: 1, SEQ ID NO: 2, SEQ ID NO: 7, and SEQ ID NO: 8.

SEQ ID NO: 7 is a one hundred nucleotide sequence representing the 5' junction between the soybean genomic DNA and the integrated transgenic expression cassette.

SEQ ID NO: 8 is a one hundred nucleotide sequence representing the 3' junction between the soybean genomic DNA and the integrated transgenic expression cassette.

SEQ ID NO: 9 is the sequence of a primer referred to as Primer SQ13570 and used to identify soybean event MON 87708. It is complimentary to the inserted expression cassette at the region close to the 3' transgene insertion border. A PCR amplicon produced from a TAQMAN® (PE Applied Biosystems, Foster City, Calif.) assay using the combination of primers SQ13570 and SQ13571 (SEQ ID NO: 10) is a positive result for the presence of the event MON 87708.

SEQ ID NO: 10 is the sequence of a primer referred to as Primer SQ13571 and used to identify soybean event MON 87708. It is complimentary to a 3' region flanking the inserted expression cassette and close to the transgene DNA insertion border. A PCR amplicon produced from a TAQ-MAN® (PE Applied Biosystems, Foster City, Calif.) assay using the combination of primers SQ13570 (SEQ ID NO: 9) and SQ13571 is a positive result for the presence of the event MON 87708.

SEQ ID NO: 11 is the sequence of a probe referred to as Probe PB4655 and used to identify soybean event MON 87708. It is complimentary to a region spanning the 3' junction of the inserted expression cassette and the genomic DNA. This probe is a 6-FAM™-labeled synthetic oligonucleotide. Release of a fluorescent signal in an amplification reaction using primers SQ13570 and SQ13571 (SEQ ID NO: 9-10) in combination with 6-FAM™-labeled probe PB4655 is diagnostic of event MON 87708 in a TAQMAN® assay.

SEQ ID NO: 12 is the sequence of a primer referred to as Primer SQ20632 and used to identify MON 87708 event zygosity.

SEQ ID NO: 13 is the sequence of a primer referred to as Primer SQ20636 and used to identify soybean wild-type and MON 87708 event zygosity.

SEQ ID NO: 14 is the sequence of a primer referred to as Primer SQ20637 and used to identify soybean wild-type zygosity.

SEQ ID NO: 15 is the sequence of a probe referred to as Probe PB10130 and used for a MON 87708 event zygosity assay.

SEQ ID NO: 16 is the sequence of a probe referred to as Probe PB10131 and used for a soybean wild-type zygosity assay.

DETAILED DESCRIPTION

The following definitions and methods are provided to better define the invention and to guide those of ordinary skill in the art in the practice of the invention. Unless otherwise noted, terms are to be understood according to conventional usage by those of ordinary skill in the relevant art.

The invention provides a transgenic soybean event MON 87708 that exhibits commercially acceptable tolerance to applications of dicamba herbicide. The event comprises a single insertion of transgenic DNA into the chromosome/genome of the soybean germplasm. An "event" is produced by: (i) transformation of a plant cell with a nucleic acid construct that includes a transgene of interest, (ii) regeneration of a population of plants resulting from the insertion of the transgene into the genome of the plant, and (iii) selection of a particular plant characterized by insertion of the transgene into a particular location in the plant's genome. The term "event" refers to the original transformant that includes the transgene inserted into the particular location in the plant's genome. The term "event" also refers to progeny of the transformant that include the transgene inserted into the particular location in the plant's genome. Such progeny may be produced by a sexual outcross between the transformant, or its progeny, and another plant. Such other plant may be a transgenic plant comprising the same or different transgene and/or a nontransgenic plant, such as one from a different variety. Even after repeated back-crossing to a recurrent parent, the inserted DNA and flanking DNA from the transformed parent is present in the progeny of the cross at the same genomic location.

As used herein, the term "soybean" means *Glycine max* and includes all plant varieties that can be bred with soybean, including wild soybean species as well as those plants belonging to *Glycine* that permit breeding between species.

The term "event" also refers to a DNA molecule from the original transformant comprising the inserted DNA and the flanking soybean genomic DNA immediately adjacent to either side of the inserted DNA. This DNA molecule is created by the act of inserting the transgenic DNA into the genome of the soybean plant, i.e., by the act of transformation. This DNA molecule therefore comprises a nucleotide sequence that is both specific to the event and that is unique to the genome of the soybean plant into which the transgenic DNA has been inserted, in that this nucleotide sequence contains both the sequence of a particular region of soybean genomic DNA and of the transgenic DNA insert. The arrangement of the inserted DNA in soybean event MON 87708 in relation to the surrounding soybean plant genome DNA is therefore specific and unique for soybean event MON 87708. This DNA molecule is also an integral part of the soybean chromosome of event MON 87708 and as such is static in the plant and may be passed on to progeny of the plant.

Event MON 87708 comprises a transgene that confers tolerance to applications of dicamba herbicide to the soybean plant. "Dicamba" refers to 3,6-dichloro-2-methoxybenzoic acid. Dicamba is a synthetic auxin herbicide useful for controlling broadleaf weeds. Soybean plants were transformed with dicamba mono-oxygenase (DMO), an enzyme cloned from *Stenotrophomonas maltophilia* which is commonly found in soil rhizosphere. Dicamba mono-oxygenase is an enzyme that catalyzes the deactivation of dicamba via an O-demethylation reaction to the nonherbicidal compound 3,5-dichlorosalicylic acid. In some areas of the world toxic weed species seeds may contaminate harvested soybean seeds that can affect the health and nutrition of animals fed the contaminated soybean commodity products. These plants can be eliminated from a soybean field by treatment with a dicamba herbicide. Members of this group of toxic weeds include *Cardaria* spp, *Heliotropium* spp, *Centaurea* spp., *Senecio* spp., *Crotalaria* spp., *Solanum* spp., *Xanthium* spp., *Amsinckia* spp., *Cassia* spp., *Sesbania* spp., *Datura* spp., *Ricinus* spp., *Argemone* spp., *Corchorus* spp., *Impomoea* spp., and *Echium* spp.

As used herein, the term "recombinant" refers to a form of DNA and/or protein and/or an organism that would not normally be found in nature and as such was created by human intervention. Such human intervention may produce a recombinant DNA molecule and/or a recombinant plant. As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene artificially incorporated into a host cell's genomic DNA and the associated flanking DNA of the host cell's genome. An example of a recombinant DNA molecule is a DNA molecule described herein resulting from the insertion of the transgene into the soybean genomic DNA, which may ultimately result in the expression of a recombinant RNA and/or protein molecule in that organism. As used herein, a "recombinant plant" is a plant that would not normally exist in nature, is the result of human intervention, and contains a transgene and/or heterologous DNA molecule incorporated into its genome. As a result of such genomic alteration, the recombinant plant is distinctly different from the related wildtype plant. An example of a recombinant plant is a soybean plant described herein as Event MON 87708.

As used herein, the term "transgene" refers to a nucleotide molecule artificially incorporated into a host cell's genome. Such transgene may be heterologous to the host cell. The term "transgenic plant" refers to a plant comprising such a transgene.

As used herein, the term "heterologous" refers to a first molecule not normally found in combination with a second molecule in nature. For example, a molecule may be derived from a first species and inserted into the genome of a second species. The molecule would thus be heterologous to the host and artificially incorporated into a host cell's genome.

As used herein, the term "chimeric" refers to a single DNA molecule produced by fusing a first DNA molecule to a second DNA molecule, where neither first nor second DNA molecule would normally be found in that configuration, i.e., fused to the other. The chimeric DNA molecule is thus a new DNA molecule not otherwise normally found in nature.

The invention provides DNA molecules and their corresponding nucleotide sequences. As used herein, the term "DNA", "DNA molecule", "nucleotide molecule" refers to a DNA molecule of genomic or synthetic origin, i.e., a polymer of deoxyribonucleotide bases or a polynucleotide molecule, read from the 5' (upstream) end to the 3' (downstream) end. As used herein, the term "DNA sequence", "nucleotide sequence" or "polynucleotide sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3. By convention, the nucleotide sequences of the invention provided as SEQ ID NO: 1-8 and fragments thereof are disclosed with reference to only one strand of the two complementary nucleotide sequence strands. By implication, the complementary sequences (i.e. the sequences of the complementary strand), also referred to in the art as the reverse complementary sequences, are within the scope of the invention and are expressly intended to be within the scope of the subject matter claimed.

The nucleotide sequence corresponding to the complete nucleotide sequence of the inserted transgenic DNA and substantial segments of the soybean genome DNA flanking either end of the inserted transgenic DNA is provided herein as SEQ ID NO: 6. A subsection of this is the inserted transgenic DNA provided as SEQ ID NO: 5. The nucleotide sequence of the soybean genome DNA physically linked by phosphodiester bond linkage to and therefore flanking the 5' end of the inserted transgenic DNA is set forth as shown in SEQ ID NO: 3. The nucleotide sequence of the soybean genome DNA physically linked by phosphodiester bond linkage to and therefore flanking the 3' end of the inserted transgenic DNA is set forth as shown in SEQ ID NO: 4.

The soybean event MON 87708 further comprises two regions, one spanning the 5' location and one spanning the 3' location where the transgenic DNA is inserted into the genomic DNA, referred to herein as the 5' and 3' junction, respectively. A "junction sequence" or "junction region" refers to the DNA sequence and/or corresponding DNA molecule that spans the inserted transgenic DNA and the adjacent flanking genomic DNA. The junction sequences may be arbitrarily represented by the two 60 nucleotide sequences provided as SEQ ID NO: 1 and SEQ ID NO: 2, each representing 30 nucleotides of the flanking genomic DNA adjacent to and contiguous with 30 nucleotides of insert DNA. Alternatively, the junction sequences may be arbitrarily represented by the two 100 nucleotide sequences provided as SEQ ID NO: 7 and SEQ ID NO: 8, each representing 50 nucleotides of the flanking genomic DNA adjacent to and contiguous with 50 nucleotides of insert DNA. These nucleotides are connected by phosphodiester linkage and in soybean event MON 87708 are present as part of the genome. In soybean the identification of one or more of SEQ ID NO: 1, SEQ ID NO: 2, SEQ ID NO: 7, and SEQ ID NO: 8 in a sample derived from a soybean plant, seed, or plant part is determinative that the DNA was obtained from soybean event MON 87708 and is diagnostic for the presence in a sample of DNA from soybean event MON 87708. The invention thus provides a DNA molecule that contains at least the nucleotide sequence as set forth in SEQ ID NO: 1, SEQ ID NO: 2, SEQ ID NO: 7, and/or SEQ ID NO: 8. Any segment of DNA derived from transgenic soybean event MON 87708 that is sufficient to include SEQ ID NO: 1, SEQ ID NO: 2, SEQ ID NO: 7, and/or SEQ ID NO: 8 is within the scope of The invention. In addition, any polynucleotide comprising a sequence complementary to any of the sequences described within this paragraph is within the scope of the invention. FIG. 1 illustrates the physical arrangement of SEQ ID NO: 1-5 and 7-8 relative to SEQ ID NO: 6 arranged from 5' to 3'.

The invention provides exemplary DNA molecules that can be used either as primers or probes for diagnosing the presence of DNA derived from soybean plant event MON 87708 in a sample. Such primers or probes are specific for a target nucleic acid sequence and as such are useful for the identification of soybean event MON 87708 nucleic acid sequence by the methods of the invention described herein.

A "primer" is typically a highly purified, isolated polynucleotide that is designed for use in specific annealing or hybridization methods that involve thermal amplification. A pair of primers may be used with template DNA, such as a sample of soybean genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. An amplicon of the invention comprises at least SEQ ID NO: 1, SEQ ID NO: 2, SEQ ID NO: 7, and/or SEQ ID NO: 8. A primer is typically designed to hybridize to a complementary target DNA strand to form a hybrid between the primer and the target DNA strand, and the presence of the primer is a point of recognition by a polymerase to begin extension of the primer (i.e., polymerization of additional nucleotides into a lengthening nucleotide molecule) using as a template the target DNA strand. Primer pairs, as used in the invention, are intended to refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO: 9-10. The primer pair provided as SEQ ID NO: 9 and SEQ ID NO: 10 are useful as a first DNA molecule and a second DNA molecule that is different from the first DNA molecule, and both are each of sufficient length of contiguous nucleotides of either SEQ ID NO: 4, SEQ ID NO: 5, or SEQ ID NO: 6 to function as DNA primers that, when used together in a thermal amplification reaction with template DNA derived from soybean event MON 87708, produce an amplicon comprising SEQ ID NO: 2.

A "probe" is an isolated nucleic acid that is complementary to a strand of a target nucleic acid. Probes according to the invention include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. An exemplary DNA molecule useful as a probe is provided as SEQ ID NO: 11.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from soybean event MON 87708 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985). As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

As used herein, the term "isolated" refers to at least partially separating a molecule from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying soybean event MON 87708, selecting plant varieties or hybrids comprising soybean event MON 87708, detecting the presence of DNA derived from the transgenic soybean event MON 87708 in a sample, and monitoring samples for the presence and/or absence of soybean event MON 87708 or plant parts derived from soybean event MON 87708.

The invention provides soybean plants, progeny, seeds, plant cells, plant parts (such as pollen, ovule, pod, flower tissue, root tissue, stem tissue, and leaf tissue), and commodity products. These plants, progeny, seeds, plant cells, plant parts, and commodity products contain a detectable amount of a polynucleotide of the invention, i.e., such as a polynucleotide having at least one of the sequences provided as SEQ ID NO: 1-8. Plants, progeny, seeds, plant cells, and plant parts of the invention may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a soybean plant lacking such additional transgene.

The invention provides soybean plants, progeny, seeds, plant cells, and plant part such as pollen, ovule, pod, flower, root or stem tissue, and leaves derived from a transgenic soybean plant event MON 87708. A representative sample of soybean event MON 87708 seed has been deposited according to the Budapest Treaty for the purpose of enabling the invention. The repository selected for receiving the deposit is the American Type Culture Collection (ATCC) having an address at 10801 University Boulevard, Manassas, Va. USA, Zip Code 20110. The ATCC repository has assigned the accession No. PTA-9670 to the event MON 87708 seed.

The invention provides a microorganism comprising a DNA molecule having SEQ ID NO: 1 and SEQ ID NO: 2 present in its genome. An example of such a microorganism is a transgenic plant cell. Microorganisms, such as a plant cell of The invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event DNA, including the transgene, to progeny. As used herein, "progeny" includes any plant, seed, plant cell, and/or regenerable plant part comprising the event DNA derived from an ancestor plant and/or a polynucleotide having at least one of the sequences provided as SEQ ID NO: 1 and SEQ ID NO: 2. Plants, progeny, and seeds may be homozygous or heterozygous for the transgene. Progeny may be grown from seeds produced by a soybean event MON 87708 plant and/or from seeds produced by a plant fertilized with pollen from a soybean event MON 87708 plant.

Progeny plants may be self-pollinated (also known as "selfing") to generate a true breeding line of plants, i.e., plants homozygous for the transgene. Selfing of appropriate progeny can produce plants that are homozygous for both added, exogenous genes.

Alternatively, progeny plants may be outcrossed, e.g., bred with another unrelated plant, to produce a varietal or a hybrid seed or plant. The other unrelated plant may be transgenic or nontransgenic. A varietal or hybrid seed or plant of the invention may thus be derived by crossing a first parent that lacks the specific and unique DNA of the soybean event MON 87708 with a second parent comprising soybean event MON 87708, resulting in a hybrid comprising the specific and unique DNA of the soybean event MON 87708. Each parent can be a hybrid or an inbred/varietal, so long as the cross or breeding results in a plant or seed of the invention, i.e., a seed having at least one allele containing the specific and unique DNA of soybean event MON 87708 and/or SEQ ID NO: 1 and SEQ ID NO: 2. Two different transgenic plants may thus be mated to produce hybrid offspring that contain two independently segregating, added, exogenous genes. For example, the MON 87708 dicamba tolerant soybean can be crossed with other transgenic soybean plant to produce a plant having the characteristics of both transgenic parents. One example of this would be a cross of MON 87708 dicamba tolerant soybean with a plant having one or more additional traits such as herbicide tolerance (e.g., soybean event 40-3-2 or soybean event MON89788 (U.S. Patent Application Publication No. 20060282915)), insect control (e.g. soybean event MON87701 (U.S. Patent Application Publication No. 20090130071)), and/or other desirable traits (e.g. enhanced oil composition such as soybean event MON87769 (PCT Patent Publication WO2009102873)), resulting in a progeny plant or seed that is tolerant to dicamba and has one or more additional traits. Herbicides for which transgenic plant tolerance has been demonstrated and the method of the invention can be applied, include but are not limited to: glyphosate, glufosinate, sulfonylureas, imidazolinones, bromoxynil, delapon, cyclohexanedione, protoporphyrionogen oxidase inhibitors, and isoxasflutole herbicides. Nucleotide molecules encoding proteins involved in herbicide tolerance are known in the art and include, but are not limited to, a nucleotide molecule encoding: glyphosate-tolerant 5-enolpyruvylshikimate-3-phosphate synthase (EPSPS) (see, for example, U.S. Pat. Nos. 5,627,061; 5,633,435; 6,040,497; 5,094,945; 5,804,425; 6,248,876; 7,183,110; RE39,247); glyphosate oxidoreductase (GOX) (see, for example, U.S. Pat. No. 5,776,760); glyphosate-n-acetyltransferase (GAT); an herbicide-tolerant acetolactate synthase (ALS, also known as acetohydroxyacid synthase (AHAS)) for tolerance to sulfonylureas, imidazolinones, triazolopyrimidines, pyrimidinyl oxybenzoates, sulfonylamino carbonyl triazolinones, and/or heteroaryl ethers; an herbicide-tolerant acetyl coenzyme A carboxylase (ACCase) or R-2,4-dichlorophenoxypropionate dioxygenase (rdpA) for tolerance to an aryloxyphenoxypropionate (AOPP) (such as haloxyfop, quizalofop, dichlorofop, and diclofop); a detoxification protein such as a 2,4-D dioxygenase (tfdA), R-2,4-dichlorophenoxypropionate dioxygenase (rdpA), AryloxyAlkanoate Dioxygenase (AAD), and/or S-2,4-dichorprop dioxygenase (sdpA) for tolerance to synthetic auxin herbicides; a bromoxynil nitrilase (Bxn) for Bromoxynil tolerance (see, for example, U.S. Pat. No. 4,810,648); a phytoene desaturase (crtI) for tolerance to norflurazon; the bialaphos resistance (bar) or phosphinothricin acetyltransferase (PAT) protein (see, for example, U.S. Pat. Nos. 5,646,024 and 5,276,268) for tolerance to glufosinate and bialaphos; and a protein for triketone (mezotrione, tembotrione, topromezone, isoxazole) herbicide-tolerance such as tolerant 4-HydroxyPhenylPyruvate Dioxygenase (HPPD), a detoxifying cytochrome P450, or an HPPD pathway bypass such as *Artbrobacter globiformis* HPP oxidase (HPPO) and *Pseudomonas acidovorans* 4-HPA 1-hydroxylase (HPAH) and NADH oxidoreductase (HPAC).

Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcox J. ed., American Society of Agronomy, Madison Wis. (1987).

The invention provides a plant part that is derived from soybean event MON 87708. As used herein, a "plant part" refers to any part of a plant which is comprised of material derived from a soybean event MON 87708 plant. Plant parts include but are not limited to pollen, ovule, pod, flower, root or stem tissue, fibers, and leaves. Plant parts may be viable, nonviable, regenerable, and/or nonregenerable.

The invention provides a commodity product that is derived from soybean event MON 87708. As used herein, a "commodity product" refers to any composition or product which is comprised of material derived from a soybean event MON 87708 plant, seed, plant cell, or plant part. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. The soybean event MON 87708 can thus be used to manufacture any commodity product typically acquired from soybean. Any such commodity product that is derived from the soybean event MON 87708 may contain at least a detectable amount of the specific and unique DNA corresponding to soybean event MON 87708, and specifically may contain a detectable amount of a polynucleotide containing at least 15 contiguous nucleotides of SEQ ID NO: 1 or SEQ ID NO: 2. Any standard method of detection for nucleotide molecules may be used, including methods of detection disclosed herein. A commodity product is within the scope of the invention if there is any detectable amount of SEQ ID NO: 1 or SEQ ID NO: 2 in the commodity product.

The plants, progeny, seeds, plant cells, plant parts (such as pollen, ovule, pod, flower, root or stem tissue, and leaves), and commodity products of the invention are therefore useful for, among other things, growing plants for the purpose of producing seed and/or plant parts of soybean event MON 87708 for agricultural purposes, producing progeny of soybean event MON 87708 for plant breeding and research purposes, use with microbiological techniques for industrial and research applications, and sale to consumers.

The invention provides methods for controlling weeds and methods for producing plants using dicamba herbicide and soybean event MON 87708. A method for controlling weeds in a field is provided and consists of planting soybean event MON 87708 varietal or hybrid plants in a field and applying a herbicidally effective dose of dicamba to the field for the purpose of controlling weeds in the field without injuring the MON 87708 plants. Such application of dicamba herbicide may be pre-emergence, i.e., any time after MON 87708 seed is planted and before MON 87708 plants emerge, or post-emergence, i.e., any time after MON 87708 plants emerge. Another method for controlling weeds in a field is also provided and consists of applying an effective dose of dicamba herbicide to control weeds in a field and then planting soybean event MON 87708 in the field. Such application of dicamba herbicide would be pre-planting, i.e., before MON 87708 seed is planted, and could be done any time pre-planting including, but not limited to, about 14 days pre-planting to about 1 day pre-planting. The invention also provides a method for producing soybean seed essentially free of the seeds of toxic weed species by planting seeds of a dicamba tolerant soybean variety MON 87708 in a field, applying a post-emergence effective dose of dicamba herbicide sufficient to kill the toxic weed species to the field, and harvesting seed from the field. A herbicidally effective dose of dicamba for use in the field should consist of a range from about 0.005 pounds per acre to about 8 pounds of dicamba per acre over a growing season. Multiple applications of dicamba may be used over a growing season, for example, two applications (such as a pre-planting application and a post-emergence application or a pre-emergence application and a post-emergence application) or three applications (such as a pre-planting application, a pre-emergence application, and a post-emergence application).

Methods for producing an herbicide tolerant soybean plant comprising the DNA sequences specific and unique to the transgenic event MON 87708 of the invention are provided. Transgenic plants used in these methods may be homozygous or heterozygous for the transgene. Progeny plants produced by these methods may be varietal or hybrid plants; may be grown from seeds produced by a soybean event MON 87708 plant and/or from seeds produced by a plant fertilized with pollen from a soybean event MON 87708 plant; and may be homozygous or heterozygous for the transgene. Progeny plants may be subsequently self-pollinated to generate a true breeding line of plants, i.e., plants homozygous for the transgene, or alternatively may be outcrossed, e.g., bred with another unrelated plant, to produce a varietal or a hybrid seed or plant.

A soybean plant that tolerates application of dicamba herbicide may be produced by sexually crossing an event MON 87708 plant comprising a nucleotide molecule comprising the sequence of SEQ ID NO: 1 and SEQ ID NO: 2 with another soybean plant and thereby producing seed, which is then grown into progeny plants. These progeny plants may then be treated with dicamba herbicide to select for progeny plants that are tolerant to dicamba herbicide. Alternatively, these progeny plants may be analyzed using diagnostic methods to select for progeny plants that contain the event MON 87708 DNA. The other plant used in the crossing may or may not be tolerant to dicamba herbicide and may or may not be transgenic. The progeny plant and/or seed produced may be varietal or hybrid seed. In practicing this method, the step of sexually crossing one plant with another plant, i.e., cross-pollinating, may be accomplished or facilitated by human intervention, for example: by human hands collecting the pollen of one plant and contacting this pollen with the style or stigma of a second plant; by human hands and/or actions removing, destroying, or covering the stamen or anthers of a plant (e.g., by detasseling or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma (e.g., in soy which naturally has flowers that hinder or prevent cross-pollination, making them naturally obligate self-pollinators without human intervention); by selective placement of plants (e.g., intentionally planting plants in pollinating proximity); and/or by application of chemicals to precipitate flowering or to foster receptivity (of the stigma for pollen).

A soybean plant that tolerates application of dicamba herbicide may be produced by selfing an event MON 87708 plant comprising a nucleotide molecule comprising the sequence of SEQ ID NO: 1 and SEQ ID NO: 2 and thereby producing seed, which is then grown into progeny plants. These progeny plants may then be treated with dicamba herbicide to select for progeny plants that are tolerant to dicamba herbicide. Alternatively, these progeny plants may be analyzed using diagnostic methods to select for progeny plants that contain the event MON 87708 DNA. In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

Progeny soybean plants and seeds encompassed by these methods and produced by using these methods will be distinct from other soybean plants, for example because the progeny soybean plants and seeds: are recombinant and as such created by human intervention; are dicamba herbicide tolerant; contain at least one allele that consists of the transgene DNA of the invention; and/or contain a detectable amount of a polynucleotide sequence selected from the group consisting of SEQ ID NO: 1 and SEQ ID NO: 2. A seed may be selected from an individual progeny plant, and so long as the seed comprises SEQ ID NO: 1 and SEQ ID NO: 2, it will be within the scope of the invention.

In practicing the invention, two different transgenic plants can be crossed to produce hybrid offspring that contain two independently segregating heterologous genes. Selfing of appropriate progeny can produce plants that are homozygous for both genes. Back-crossing to a parental plant and out-crossing with a non-transgenic plant are also contemplated, as is vegetative propagation. Descriptions of other methods that are commonly used for different traits and crops can be found in one of several references, e.g., Fehr, in Breeding Methods for Cultivar Development, Wilcox J. ed., American Society of Agronomy, Madison Wis. (1987).

The plants and seeds used in the methods disclosed herein may also contain one or more additional transgenes. Such transgene may be any nucleotide sequence encoding a protein or RNA molecule conferring a desirable trait including but not limited to increased insect resistance, increased water use efficiency, increased yield performance, increased drought resistance, increased seed quality, improved nutritional quality, and/or increased herbicide tolerance, in which the desirable trait is measured with respect to a soybean plant lacking such additional transgene.

The methods of the invention are therefore useful for, among other things, controlling weeds in a field while growing plants for the purpose of producing seed and/or plant parts of soybean event MON 87708 for agricultural or research purposes, selecting for progeny of soybean event MON 87708 for plant breeding or research purposes, and producing progeny plants and seeds of soybean event MON 87708.

The plants, progeny, seeds, plant cells, plant parts (such as pollen, ovule, pod, flower, root or stem tissue, and leaves), and commodity products of the invention may be evaluated for DNA composition, gene expression, and/or protein expression. Such evaluation may be done by using any standard method such as PCR, northern blotting, southern analysis, western blotting, immuno-precipitation, and ELISA or by using the methods of detection and/or the detection kits provided herein.

Methods of detecting the presence of DNA derived from a soybean cell, tissue, seed, or plant of soybean event MON 87708 in a sample are provided. One method consists of (i) extracting a DNA sample from at least one soybean cell, tissue, seed, or plant, (ii) contacting the DNA sample with a primer pair that is capable of producing an amplicon from event MON 87708 DNA under conditions appropriate for DNA amplification, (iii) performing a DNA amplification reaction, and then (iv) detecting the amplicon molecule and/or confirming that the nucleotide sequence of the amplicon comprises a nucleotide sequence specific for event MON 87708, such as one selected from the group consisting of SEQ ID NO: 1-8. The amplicon should be one that is specific for event MON 87708, such as an amplicon that comprises SEQ ID NO: 1 or SEQ ID NO: 2. The detection of a nucleotide sequence specific for event MON 87708 in the amplicon is determinative and/or diagnostic for the presence of the soybean event MON 87708 specific DNA in the sample. An example of a primer pair that is capable of producing an amplicon from event MON 87708 DNA under conditions appropriate for DNA amplification is provided as SEQ ID NO: 10-11. Other primer pairs may be readily designed by one of skill in the art and would comprise at least one fragment of SEQ ID NO: 6. Another method of detecting the presence of DNA derived from a soybean cell, tissue, seed, or plant of soybean event MON 87708 in a sample consists of (i) extracting a DNA sample from at least one soybean cell, tissue, seed, or plant, (ii) contacting the DNA sample with a DNA probe specific for event MON 87708 DNA, (iii) allowing the probe and the DNA sample to hybridize under stringent hybridization conditions, and then (iv) detecting hybridization between the probe and the target DNA sample. An example of the sequence a DNA probe that is specific for event MON 87708 DNA is provided as SEQ ID NO: 11. Other probes may be readily designed by one of skill in the art and would comprise at least one fragment of SEQ ID NO: 6. Detection of probe hybridization to the DNA sample is diagnostic for the presence of soybean event MON 87708 specific DNA in the sample. Absence of hybridization is alternatively diagnostic of the absence of soybean event MON 87708 specific DNA in the sample.

DNA detection kits are provided that are useful for the identification of soybean event MON 87708 DNA in a sample and can also be applied to methods for breeding soybean plants containing the appropriate event DNA. Such kits contain DNA primers and/or probes comprising fragments of SEQ ID NO: 1-8. One example of such a kit comprises at least one DNA molecule of sufficient length of contiguous nucleotides of SEQ ID NO: 6 to function as a DNA probe useful for detecting the presence and/or absence of DNA derived from transgenic soybean event MON 87708 in a sample. The DNA derived from transgenic soybean event MON 87708 would comprise SEQ ID NO: 1, SEQ ID NO: 2, SEQ ID NO: 7, and/or SEQ ID NO: 8. A DNA molecule sufficient for use as a DNA probe is provided that is useful for determining, detecting, or diagnosing the presence and/or absence of soybean event MON 87708 DNA in a sample is provided as SEQ ID NO: 11. Other probes may be readily designed by one of skill in the art and should comprise at least 15 contiguous nucleotides of SEQ ID NO: 6 and be sufficiently unique to soybean event MON 87708 DNA in order to identify DNA derived from the event. Another type of kit comprises a primer pair useful for producing an amplicon useful for detecting the presence and/or absence of DNA derived from transgenic soybean event MON 87708 in a sample. Such a kit would employ a method comprising contacting a target DNA sample with a primer pair as described herein, then performing a nucleic acid amplification reaction sufficient to produce an amplicon comprising SEQ ID NO: 1, SEQ ID NO: 2, SEQ ID NO: 7, and/or SEQ ID NO: 8, and then detecting the presence and/or absence of the amplicon. Such a method may also include sequencing the amplicon or a fragment thereof, which would be determinative of, i.e. diagnostic for, the presence of the soybean event MON 87708 specific DNA in the target DNA sample. Other primer pairs may be readily designed by one of skill in the art and should comprise at least 15 contiguous nucleotides of SEQ ID NO: 6 and be sufficiently unique to soybean event MON 87708 DNA in order to identify DNA derived from the event.

Nucleic-acid amplification can be accomplished by any of the various nucleic-acid amplification methods known in the art, including thermal amplification methods. Many techniques are known in the art for detecting, quantifying, and/or sequencing the amplicon produced by these methods. One exemplary technique useful in practicing this invention is TAQMAN® (PE Applied Biosystems, Foster City, Calif.).

The kits and detection methods of the invention are useful for, among other things, identifying soybean event MON 87708, selecting plant varieties or hybrids comprising soybean event MON 87708, detecting the presence of DNA derived from the transgenic soybean event MON 87708 in a sample, and monitoring samples for the presence and/or absence of soybean event MON 87708 or plant parts derived from soybean event MON 87708.

The sequence of the heterologous DNA insert, junction sequences, or flanking sequences from soybean event MON 87708 (with representative seed samples deposited as ATCC PTA-9670) can be verified (and corrected if necessary) by amplifying such sequences from the event using primers derived from the sequences provided herein followed by standard DNA sequencing of the amplicon or of the cloned DNA.

As used herein, the term "comprising" means "including but not limited to".

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Soybean A3525 and MON 87708 Event Selection

The soybean plant MON 87708 was produced by *Agrobacterium*-mediated transformation of soybean. Soybean cells were transformed and regenerated into intact soybean plants and individual plants were selected from the population of plants that showed integrity of the plant expression cassette and resistance to dicamba. From this population, soybean plant event MON 87708 was selected and characterized.

The transgenic dicamba tolerant soybean plant MON 87708 was developed through *Agrobacterium*-mediated transformation of soybean meristem tissue utilizing transformation vector PV-GMHT4355. The method was described in U.S. Pat. No. 6,384,301 (herein incorporated by reference), which allows for the generation of transformed plants without utilization of callus. Briefly, meristem tissues were excised from the embryos of germinated A3525 soybean seed (Asgrow, St Louis, Mo.). After co-culturing with *Agrobacterium* carrying the vector, the meristems were placed on selection medium containing glyphosate (Monsanto, St Louis, Mo.), carbenicillin disodium salt, cefotaxime sodium salt, and ticarcillin disodium salt/potassium clavulanate mixture to inhibit the growth of untransformed plant cells and excess *Agrobacterium*. The meristems were then placed in media conducive to shoot and root development. Rooted plants with normal phenotypic characteristics were selected and transferred to soil for growth and further assessment.

The R0 plants generated through the above transformation were transferred to soil for growth and then selfed to produce R1 seed. During subsequent selfing of the R0 plants to produce the R1 generation, the unlinked insertions of T-DNA I (dmo expression cassette) and T-DNA II (cp4 epsps expression cassette) were segregated. A non-lethal dose of glyphosate was applied to R1 plants. The plants with minor injuries were selected for further analyses, whereas plants showing no injury, i.e., containing T-DNA II (cp4 epsps expression cassette) were eliminated from subsequent development. Subsequently, R0 plants containing only a single T-DNA I insert (i.e., dmo gene cassette) were identified. The T-DNA I expression cassette comprised the Peanut Chlorotic Streak Virus (PClSV) promoter with a duplicated enhancer region (P-PClSV.FLt-enh); operably linked to a DNA leader derived from RNA transcript of Tobacco Etch Virus (L-TEV); operably linked to a DNA molecule encoding an N-terminal chloroplast transit peptide from ribulose 1,5-bisphosphate carboxylase small subunit (SSU) from *Pisum sativum* (TS-RbcS-3C); operably linked to part of the mature protein from ribulose 1,5-bisphosphate carboxylase small subunit (SSU) from *Pisum sativum* (CR-RbcS-3C); operably linked to a DNA molecule encoding a dicamba monooxygenase (DMO) from *Stenotrophomonas maltophilia* (*Pseudomonas maltophilia* was the original name of the source of the DMO gene. This source organism was subsequently reclassified first as *Xanthomonas maltophilia* and then as *Stenotrophomonas maltophilia*); operably linked to a 3' UTR DNA molecule derived from the ribulose 1,5-bisphosphate carboxylase small subunit gene of *Pisum sativum* (T-Ps.RbcS2-E9). Plants were selected by a combination of analytical techniques, including TaqMan, PCR analysis, and herbicide spray. The MON 87708 event was selected from among approximately 2,400 individual transgenic events based on its superior phenotypic characteristics, a comprehensive molecular profile analysis, and its desirable haplotype association. Event MON 87708 was then crossed with event MON 89788 (glyphosate tolerant). The progeny of this cross were treated with dicamba (Clarity®, BASF, Research Triangle Park, N.C.), glyphosate (Roundup WeatherMAX®, Monsanto Co., St Louis, Mo.), or a combination of dicamba and glyphosate. The treatments were done at pre-plant, post-plant at the vegetative 3 growth stage (V3), and post-plant at the reproduction 1 stage (R1). Treated plants were scored for percent growth inhibition at 14 days after treatment (DAT) for the pre-plant herbicide treatment, 3 DAT for post-emergence treatment at the VE stage, and 3 DAT post-emergence treatment at the R1 stage. The herbicide(s) were applied at various rates per acre as shown in Table 1. Percent inhibition measurements represent an average of the repetitions.

TABLE 1

Dicamba and/or Roundup WeatherMAX ® tolerance testing with MON89788 x MON 87708

| Herbicide (a.e. Rate gm/ha (lb/a)) | % inhibition at 14 DAT PRE | % inhibition at 3 DAT POST (V3) | % inhibition at 3 DAT POST (R1) |
| --- | --- | --- | --- |
| Untreated/No herbicide | 0.0 | 0.0 | 0.0 |
| Roundup WeatherMAX ® (3364 (3.0)) | 0.0 | 0.0 | 0.0 |
| Clarity ® (2244 (2.0)) | 0.0 | 10.0 | 20.0 |
| Clarity ®561 (0.5) and Roundup WeatherMAX ® (841 (0.75)) | 0.0 | 5.0 | 10.0 |
| Clarity ® (1120 (1.0)) and Roundup WeatherMAX ® (1682 (1.5)) | 0.0 | 7.5 | 12.5 |
| Clarity ® (2244 (2.0)) and Roundup WeatherMAX ® (3364 (3.0)) | 0.0 | 22.5 | 25.0 |

The dicamba tolerance transgene was mapped in soybean event MON 87708 to linkage group 9 at approximately map position 143.5. The associated haplotype window 19743 and 19767 has no effect on yield, maturity, height or lodging. Haplotype association information is provided in Table 2 where GM A92205 indicates event MON 87708.

TABLE 2

Haplotype association LG9, Pos 143.5

| Event | Haplotype Window | Haplotype ID | Yield | Maturity | Height | Lodging | Haplotype sequence | Linkage group |
| --- | --- | --- | --- | --- | --- | --- | --- | --- |
| GM_A92205 | 19743 | 1573355 | 0.00 | -0.03 | 0.06 | 0.04 | CGCTG | 9 |
| GM_A92205 | 19743 | 1573357 | 0.00 | 0.07 | -0.03 | -0.04 | CGCTA | 9 |
| GM_A92205 | 19743 | 1573371 | 0.00 | -0.09 | -0.41 | -0.09 | CCCTG | 9 |
| GM_A92205 | 19743 | 1573373 | 0.00 | -0.20 | -0.01 | -0.03 | TG*GG | 9 |
| GM_A92205 | 19743 | 1573374 | 0.00 | -0.08 | -0.07 | 0.05 | TG*GA | 9 |
| GM_A92205 | 19743 | 1573375 | 0.00 | -0.15 | 0.05 | 0.04 | CCCTA | 9 |
| GM_A92205 | 19743 | 1573376 | 0.00 | -0.45 | -0.14 | 0.00 | TC*GG | 9 |
| GM_A92205 | 19767 | 1573486 | 0.00 | 0.00 | -0.03 | 0.00 | TACGGTC | 9 |
| GM_A92205 | 19767 | 1573493 | 0.00 | 0.00 | 0.22 | 0.00 | AACAATT | 9 |
| GM_A92205 | 19767 | 1573494 | 0.00 | 0.00 | 0.03 | 0.00 | TACAATC | 9 |
| GM_A92205 | 19767 | 1573495 | 0.00 | 0.00 | 0.07 | 0.00 | TGAAACC | 9 |
| GM_A92205 | 19767 | 1573497 | 0.00 | 0.00 | 0.41 | 0.00 | TACGGTT | 9 |
| GM_A92205 | 19767 | 1573499 | 0.00 | 0.00 | -0.01 | 0.00 | TGAAACT | 9 |
| GM_A92205 | 19767 | 1573500 | 0.00 | 0.00 | 0.06 | 0.00 | TGAGACC | 9 |
| GM_A92205 | 19767 | 1573502 | 0.00 | 0.00 | -0.07 | 0.00 | AACAATC | 9 |
| GM_A92205 | 19767 | 1573503 | 0.00 | 0.00 | 0.08 | 0.00 | AACGATC | 9 |
| GM_A92205 | 19767 | 1573504 | 0.00 | 0.00 | 0.07 | 0.00 | TACAGTC | 9 |
| GM_A92205 | 19767 | 1573506 | 0.00 | 0.00 | -0.03 | 0.00 | AACGATT | 9 |
| GM_A92205 | 19767 | 1573507 | 0.00 | 0.00 | 0.20 | 0.00 | TGAAATT | 9 |

Example 2

Characterization of MON 87708 DNA Sequences

The DNA inserted into the genome of soybean plant MON 87708 and the flanking sequence was characterized by detailed molecular analyses. These analyses included: the insert sequence, the insert number (number of integration sites within the soybean genome), the copy number (number of copies of transgene DNA within one locus), the integrity of the inserted gene cassette, the flanking sequences, and the association of the insertion with haplotype regions of the soybean genome.

Molecular DNA probes were used that included the intact coding region and its respective regulatory elements, the promoters, introns, and polyadenylation sequences of the plant expression cassettes. The analysis showed that MON 87708 contains a single transgene DNA insertion with one copy of the expression cassette. Inverse PCR and DNA sequence analyses were performed to determine the 5' and 3' insert-to-plant genome junctions, confirm the organization of the elements within the insert (FIG. 1), and determine the complete DNA sequence of the insert in soybean plant MON 87708 (provided herein as SEQ ID NO: 5). A soybean plant that comprises in its genome the linked transgene genetic elements shown in FIG. 1 and is resistant to dicamba is an aspect of the invention.

Sequences flanking the transgene DNA insertion in MON 87708 were determined using inverse PCR as described in Ochman et al., 1990 (PCR Protocols: A guide to Methods and Applications, Academic Press, Inc.) and/or genome walker techniques. Plant genomic DNA was isolated from both A3525 and the transgenic soybean lines from tissue grown under standard greenhouse conditions. Approximately 1 gram of young leaf tissue was combined with liquid nitrogen and ground to a fine powder using a mortar and pestle. DNA was extracted using a Nucleon™ PhytoPure™ Genomic DNA extraction kit (RPN8511, Amersham, Piscataway, N.J.) according to the manufacturer's protocol. After the final precipitation step, DNA was resuspended in 0.5 ml of TE (10 mM Tris-HCl pH 8.0, 1 mM EDTA). This method can be modified by one skilled in the art to extract DNA from any tissue of soybean, including, but not limited to seed. An aliquot of DNA was digested with restriction endonucleases selected based upon restriction analysis of the transgene DNA. After self-ligation of restriction fragments, PCR was performed using primers designed from the transgene DNA sequence that would amplify sequences extending away from the 5' and 3' ends of the transgene DNA. PCR products were separated by agarose gel electrophoresis and purified using a QIAGEN gel purification kit (Qiagen, Valencia, Calif.). The subsequent DNA products were sequenced directly using standard DNA sequencing protocols. The 5' flanking sequence which extends into the right border sequence of the expression cassette transgene DNA is presented as SEQ ID NO: 3 ([C], see FIG. 1). The 3' flanking sequence which extends into the left border sequence of the expression cassette transgene DNA is presented as SEQ ID NO: 4 ([D], see FIG. 1). The portion of the expression cassette DNA that was fully integrated into the A3525 genomic DNA is presented as SEQ ID NO: 5 ([E], see FIG. 1).

Isolated DNA molecule sequences were compared to the transgene DNA sequence to identify the flanking sequence and the co-isolated transgene DNA fragment. Confirmation of the presence of the expression cassette was achieved by PCR with primers designed based upon the deduced flanking sequence data and the known transgene DNA sequence. The wild type sequence corresponding to the same region in which the transgene DNA was integrated in the transformed line was isolated using primers designed from the flanking sequences in MON 87708. The PCR reactions were performed using the Elongase® amplification system (Invitrogen, Carlsbad, Calif.). The flanking DNA sequences in MON 87708 and the A3525 wild type sequence were analyzed against multiple nucleotide and protein databases. This information was used to examine the relationship of the transgene to the plant genome and to look for the insertion site integrity. The flanking sequence and wild type sequences were used to design primers for TAQMAN® endpoint assays used to identify the events. Zygosity assays were developed using this information.

Example 3

Event Specific Endpoint TAQMAN® Assays

This example describes an event specific endpoint TAQMAN® thermal amplification method developed to identify event MON 87708 in a sample. Examples of conditions useful with the event MON 87708 Specific Endpoint TAQMAN® method are as follows: Step 1: 18 megohm water adjusted for final volume of 10 µl. Step 2: 5.0 µl of 2× Universal Master Mix (dNTPs, enzyme, buffer) to a 1× final concentration. Step 3: 0.5 µl Event Primer-1 (SQ13570) and Event Primer-2 (SQ13571) Mix (resuspended in 18 megohm water to a concentration of 20 uM for each primer) to 1.0 µM final concentration (for example in a microcentrifuge tube, the following should be added to achieve 500 µl at a final concentration of 20 uM: 100 µl of Primer SQ13570 (SEQ ID NO: 9) at a concentration of 100 µM; 100 µl of Primer SQ13571 (SEQ ID NO: 10) at a concentration of 100 µM; 300 µl of 18 megohm water). Step 4: 0.2 µl Event 6-FAM™ MGB Probe PB4655 (resuspended in 18 megohm water to a concentration of 10 µM (SEQ ID NO: 11) to 0.2 µM final concentration. Step 5: 0.5 µl Internal Control Primer-1 and Internal Control Primer-2 Mix (resuspended in 18 megohm water to a concentration of 20 µM for each primer) to 1.0 µM final concentration. Step 6: 0.2 µl Internal Control VIC™ Probe to 0.2 µM final concentration (resuspended in 18 megohm water to a concentration of 10 µM) Step 7: 3.0 µl Extracted DNA (template) for each sample with one each of the following comprising 1. Leaf Samples to be analyzed; 2. Negative control (non-transgenic DNA); 3. Negative water control (no template); 4. Positive control MON 87708 DNA. Step 8: Thermocycler Conditions as follows: One Cycle at 50° C. for 2 minutes; One Cycle at 95° C. for 10 minutes; Ten Cycles of 95° C. for 15 seconds then 64° C. for 1 minute with −1° C./cycle; Thirty Cycles of 95° C. for 15 seconds then 54° C. 1 minute; final cycle of 10° C.

The DNA primers used in the endpoint assay are primers SQ13570 (SEQ ID NO: 9), SQ13571 (SEQ ID NO: 10), and 6-FAM™ labeled probe PB4655 (SEQ ID NO: 11). 6-FAM™ is a fluorescent dye product of Applied Biosystems (Foster City, Calif.) attached to the DNA probe. For TAQMAN® MGB™ probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. SQ13570 (SEQ ID NO: 9) and SQ13571 (SEQ ID NO: 10) when used with these reaction methods with PB4655 (SEQ ID NO: 11) produce a DNA amplicon that is diagnostic for event MON 87708 DNA. The controls for this analysis should include a positive control from soybean containing event MON 87708 DNA, a negative control from non-transgenic soybean, and a negative control that contains no template DNA. Additionally, a control for the PCR reaction includes Internal Control Primers and an Internal Control Probe, specific to a single copy gene in the *Glycine* genome. One of skill in the art will know how to design primers specific to a single copy gene in the *Glycine* genome. These assays are optimized for use with either an Applied Biosystems GeneAmp® PCR System 9700 (run at maximum speed) or MJ Research DNA Engine PTC-225 thermal cycler. Other methods and apparatus known to those skilled in the art that produce amplicons that identify the event MON 87708 DNA is within the skill of the art.

R0 plants demonstrating the presence of the expression cassette were allowed to develop into fully mature plants. Probes designed based on the sequences of the dicamba tolerance transgene cassette were used to probe Southern blots to determine linkage. The R0 plants were also evaluated for copy number of the expression cassette using a combination of Southern analysis and endpoint TAQMAN®.

A zygosity assay is useful for determining if a plant comprising an event is homozygous for the event DNA; that is comprising the exogenous DNA in the same location on each chromosome of a chromosomal pair; or heterozygous for an event DNA, that is comprising the exogenous DNA on only one chromosome of a chromosomal pair; or is null for the event DNA, that is wildtype. The endpoint TAQ-MAN® thermal amplification method was also used to develop zygosity assays for event MON 87708. This example describes an event specific endpoint TAQMAN® thermal amplification method developed to determine the zygosity of event MON 87708 in a sample. For this assay, a three primer assay was employed wherein primer SQ20632 (SEQ ID NO: 12) hybridizes and extends specifically from the 3' junction of the inserted exogenous DNA and genomic DNA, primer SQ20636 (SEQ ID NO: 13) hybridizes and extends specifically from the DNA flanking the 3' side of the inserted exogenous DNA, and primer SQ20637 (SEQ ID NO: 14) hybridizes and extends specifically from genomic DNA into which was integrated the inserted exogenous DNA. The three primers are diagnostic for the event. In this example, primer SQ20636 (SEQ ID NO: 13) and primer SQ20632 (SEQ ID NO: 12) and the 6-FAM™-labeled oligonucleotide probe PB10130 (SEQ ID NO: 15) are diagnostic when there is a copy of the inserted exogenous DNA. In this example, SQ20636 (SEQ ID NO: 13) and primer SQ20637 (SEQ ID NO: 14) and the VIC™-labeled oligonucleotide probe PB10131 (SEQ ID NO: 16) are diagnostic when there is no copy of the inserted exogenous DNA present in the genomic DNA, i.e. wildtype. When the three primers and two probes are mixed together in a PCR reaction with DNA extracted from a plant homozygous for event MON 87708, there is a fluorescent signal only from the 6-FAM™-labeled oligonucleotide probe PB10130 (SEQ ID NO: 15) which is indicative of and diagnostic a plant homozygous for event MON 87708. When the three primers and two probes are mixed together in a PCR reaction with DNA extracted from a plant heterozygous for event MON 87708, there is a fluorescent signal from both the 6-FAM™-labeled oligonucleotide probe PB10130 (SEQ ID NO: 15) and the VIC™-labeled oligonucleotide probe PB10131 (SEQ ID NO: 16) which is indicative of and diagnostic a plant heterozygous for event MON 87708. When the three primers and two probes are mixed together in a PCR reaction with DNA extracted from a plant which is null for event MON 87708 (i.e. wildtype), there is a fluorescent signal from only the VIC™-labeled oligonucleotide probe PB10131 (SEQ ID NO: 16) which is indicative of and diagnostic a plant null for event MON 87708, i.e. wildtype. Examples of conditions useful with this method are as follows. Step 1: 18 megohm water adjusted for final volume of 10 µl. Step 2: 5.0 µl of 2× Universal Master Mix (Applied Biosystems cat #4304437; dNTPs, enzyme, buffer) to a 1× final concentration. Step 3: 0.5 µl of Zygosity Primers SQ20632, SQ20636, SQ20637 (resuspended in 18 megohm water to a concentration of 20 µM for each primer) to a final concentration of 1.0 µM. Step 4: 0.2 µl 6-FAM™ Probe PB10130 (SEQ ID NO: 15) (resuspended in 18 megohm water to a concentration of 10 µM) to 0.2 µM final concentration. Step 5: 0.2 µl VIC™ Probe PB10131 (SEQ ID NO: 16) (resuspended in 18 megohm water to a concentration of 10 µM) to 0.2 µM final concentration. Step 6: 3.0 µl Extracted DNA (template) for each sample with one each of the following comprising 1. Leaf Samples to be analyzed (4-80 ng of genomic DNA diluted in water); 2. Negative control (non-transgenic soybean DNA; 4 ng diluted in water); 3. Negative water control (no template; solution in which DNA was resuspended); 4. Positive control MON 87708 genomic DNA from known heterozygous event (4 ng diluted in water); 5. 4. Positive control MON 87708 genomic DNA from known homozygous event (4 ng diluted in water). Step 7: Gently mix. Step 8: Thermocycler Conditions when using Applied Biosystems GeneAmp® PCR System 9700 (run at maximum speed) or MJ Research DNA Engine PTC-225 thermal cycler are as follows: One Cycle at 50° C. for 2 minutes; one cycle at 95° C. for 10 minutes; Ten Cycles of (95° C. for 15 seconds then 64° C. for 1 minute (−1° C./cycle); Thirty Cycles of (95° C. for 15 seconds then 54° C. for 1 minute); Optional additional 10 to 20 cycles (95° C. for 15 seconds then 64° C. for 1 minute (−1° C./cycle) may provide more distinct population separation during EndPoint TaqMan® analysis; One cycle at 10° C. hold.

Example 4

Identification of Event MON 87708 in any MON 87708 Breeding Activity

The following example describes how one may identify the MON 87708 event within progeny of any breeding activity using soybean event MON 87708.

DNA event primer pairs are used to produce an amplicon diagnostic for soybean event MON 87708. An amplicon diagnostic for MON 87708 comprises at least one junction sequence, provided as SEQ ID NO: 1 or SEQ ID NO: 2 or SEQ ID NO: 7 or SEQ ID NO: 8. Event primer pairs that will produce a diagnostic amplicon for MON 87708 include primer pairs based upon the flanking sequences and the inserted expression cassette. To acquire a diagnostic amplicon in which SEQ ID NO: 1 is found, one would design a forward primer molecule based upon SEQ ID NO: 3 from bases 1 through 1126 and a reverse primer molecule based upon the inserted expression cassette DNA sequence (SEQ ID NO: 5 from positions 1 through 3003) in which the primer molecules are of sufficient length of contiguous nucleotides to specifically hybridize to SEQ ID NO: 3 and SEQ ID NO: 5. To acquire a diagnostic amplicon in which SEQ ID NO: 2 is found, one would design a forward primer molecule based upon the inserted expression cassette DNA sequence (SEQ ID NO: 5 from positions 1 through 3003) and a reverse primer molecule based upon the 3' flanking sequence (SEQ ID NO: 4 from bases 131 through 1947), in which the primer molecules are of sufficient length of contiguous nucleotides to specifically hybridize to SEQ ID NO: 4 and SEQ ID NO: 5. For practical purposes, one should design primers which produce amplicons of a limited size range, for example, between 100 to 1000 bases. Smaller (shorter polynucleotide length) sized amplicons in general are more reliably produced in PCR reactions, allow for shorter cycle times, and can be easily separated and visualized on agarose gels or adapted for use in endpoint TAQ-MAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair derived from the combination of SEQ ID NO: 3 and SEQ ID NO: 5 or the combination of SEQ ID NO: 4 and SEQ ID NO: 5 that are useful in a DNA amplification method to produce an amplicon diagnostic for MON 87708 or progeny thereof is an aspect of the invention. Any single isolated DNA polynucleotide primer molecule comprising at least 11 contiguous nucleotides of SEQ ID NO: 3, or its complement that is useful in a DNA amplification method to produce an amplicon diagnostic for MON 87708 or progeny thereof is an aspect of the invention. Any single isolated DNA polynucleotide primer molecule comprising at least 11 contiguous nucleotides of SEQ ID NO: 4, or its complement that is useful in a DNA amplification method to produce an amplicon diagnostic for MON 87708 or progeny thereof is an aspect of the invention. Any single isolated DNA polynucleotide primer molecule comprising at least 11 contiguous nucleotides of SEQ ID NO: 5, or its complement that is useful in a DNA amplification method to produce an amplicon diagnostic for MON 87708 or progeny thereof is an aspect of the invention.

An example of the amplification conditions for this analysis is illustrated in Example 3. However, any modification of these methods or the use of DNA primers homologous or complementary to SEQ ID NO: 3 or SEQ ID NO: 4 or DNA sequences of the genetic elements contained in the transgene insert (SEQ ID NO: 5) of MON 87708 that produce an amplicon diagnostic for MON 87708 is within the art. A diagnostic amplicon comprises a DNA molecule homologous or complementary to at least one transgene/genomic junction DNA (SEQ ID NO: 1 or SEQ ID NO: 2 or SEQ ID NO: 7 or SEQ ID NO: 8), or a substantial portion thereof.

An analysis for event MON 87708 plant tissue sample should include a positive tissue control from event MON 87708, a negative control from a soybean plant that is not event MON 87708 (for example, but not limited to A3525), and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Example 3 may differ, but result in an amplicon diagnostic for event MON 87708 DNA. The use of these DNA primer sequences with modifications to the methods of Example 3 are within the scope of the invention. The amplicon produced by at least one DNA primer sequence derived from SEQ ID NO: 3, SEQ ID NO: 4, or SEQ ID NO: 5 that is diagnostic for MON 87708 is an aspect of the invention.

DNA detection kits contain at least one DNA primer of sufficient length of contiguous nucleotides derived from SEQ ID NO: 3, SEQ ID NO: 4, or SEQ ID NO: 5, that when used in a DNA amplification method produces a diagnostic amplicon for MON 87708 or its progeny is an aspect of the invention. A MON 87708 soybean plant, plant part, plant cell, seed, or commodity product that will produce an amplicon diagnostic for MON 87708 when tested in a DNA amplification method is an aspect of the invention. The assay for the MON 87708 amplicon can be performed by using an Applied Biosystems GeneAmp® PCR System 9700 (run at maximum speed) or MJ Research DNA Engine PTC-225 thermal cycler or any other amplification system that can be used to produce an amplicon diagnostic of MON 87708 as shown in Example 3.

A deposit of a representative sample of soybean event MON 87708 seed disclosed above and recited in the claims has been made under the Budapest Treaty with the American Type Culture Collection (ATCC), 10801 University Boulevard, Manassas, Va. 20110. The ATCC accession number for this deposit is PTA-9670. The deposit will be maintained in the depository for a period of 30 years, or 5 years after the last request, or for the effective life of the patent, whichever is longer, and will be replaced as necessary during that period.

Having illustrated and described the principles of the invention, it should be apparent to persons skilled in the art that the invention can be modified in arrangement and detail without departing from such principles. We claim all modifications that are within the spirit and scope of the appended claims.

We claim:

1. A recombinant soybean plant, seed, cell, or plant part thereof comprising the nucleotide sequence of SEQ ID NO: 1 and SEQ ID NO: 2 and a nucleic acid molecule encoding a dicamba mono-oxygenase (DMO).

2. The recombinant soybean plant, seed, cell, or plant part thereof of claim 1, wherein said plant, seed, cell, or plant part thereof is tolerant to dicamba herbicide treatment.

3. The recombinant soybean plant, seed, cell, or plant part thereof of claim 1, the genome of which produces an amplicon comprising a DNA molecule selected from the group consisting of SEQ ID NO: 1-4, SEQ ID NO: 6-8, and full complements thereof, when tested in a DNA amplification method.

4. A soybean plant or seed, wherein said soybean plant or seed comprises event MON 87708, a representative sample of seed comprising said event having been deposited under ATCC accession No. PTA-9670.

5. The soybean plant or seed of claim 4, wherein said soybean plant or seed is a hybrid having at least one parent comprising event MON 87708.

6. A nonliving plant material comprising the nucleotide sequence of SEQ ID NO: 1 and SEQ ID NO: 2 and a nucleic acid molecule encoding a dicamba mono-oxygenase (DMO).

7. A commodity product comprising the nucleotide sequence of SEQ ID NO: 1 and SEQ ID NO: 2 and a nucleic acid molecule encoding a dicamba mono-oxygenase (DMO).

8. The commodity product of claim 7, wherein said commodity product is selected from the group consisting of whole or processed seeds, animal feed, oil, meal, flour, flakes, bran, milk, cheese, paper, cream, wine, biomass, and fuel products.

9. A method for controlling weeds in a field comprising planting soybean plants comprising event MON 87708 in a field and applying an effective dose of dicamba herbicide to control weeds in said field without injuring said soybean plants comprising event MON 87708.

10. The method of claim 9, wherein said effective dose of dicamba herbicide is from about 0.005 pounds to about 8 pounds per acre.

11. A method for controlling weeds in a field comprising applying an effective dose of dicamba herbicide to control weeds in a field and then planting soybean plants comprising event MON 87708 in said field.

12. The method of claim 11, wherein said effective dose of dicamba herbicide is from about 0.005 pounds to about 8 pounds per acre and said planting soybean plants comprising event MON 87708 is within 14 days of said applying an effective dose of dicamba herbicide.

13. A method for producing soybean seed essentially free of toxic weed species seeds, said method comprising:
 a) planting soybean plants comprising event MON 87708 in a field;
 b) applying an effective dose of a dicamba herbicide to said field to kill toxic weeds in said field without injuring said soybean plants comprising event MON 87708; and
 c) harvesting soybean seed from said field.

14. The method of claim 13, wherein said toxic weed species seeds are selected from the group consisting of *Cardaria* spp, *Heliotropium* spp, *Centaurea* spp., *Senecio* spp., *Crotalaria* spp., *Solanum* spp., *Xanthium* spp., *Amsinckia* spp., *Cassia* spp., *Sesbania* spp., *Datura* spp., *Ricinus* spp., *Argemone* spp., *Corchorus* spp., *Impomoea* spp., and *Echium* spp.

15. A method of producing a soybean plant that tolerates application of dicamba herbicide comprising:
 a) sexually crossing a transgenic soybean plant comprising event MON 87708 comprising a nucleotide molecule having a nucleotide sequence selected from the group consisting of SEQ ID NO: 1-4, SEQ ID NO: 6-8, and full complements thereof, with a second soybean plant;

b) collecting the seed produced from said cross;
c) growing said seed to produce a plurality of progeny plants;
d) treating said plurality of progeny plants with dicamba; and
e) selecting a progeny plant that is tolerant to dicamba.

16. A method of producing a soybean plant that tolerates application of dicamba herbicide comprising:
a) selfing a transgenic soybean plant comprising event MON 87708 comprising a nucleotide molecule having a nucleotide sequence selected from the group consisting of SEQ ID NO: 1-4, SEQ ID NO: 6-8, and full complements thereof;
b) collecting the seed produced from said selfing;
c) growing said seed to produce a plurality of progeny plants;
d) treating said plurality of progeny plants with dicamba; and
e) selecting a progeny plant that is tolerant to dicamba.

* * * * *

SEQUENCE LISTING

```
<160> NUMBER OF SEQ ID NOS: 16

<210> SEQ ID NO 1
<211> LENGTH: 60
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 1
ttgatctcca tgagccattt agtctcacct tcaaacactg atagtttaaa ctgaaggcgg      60

<210> SEQ ID NO 2
<211> LENGTH: 60
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 2
tcattgctga tccatgtaga tttcccggac tttagctcaa aatgcatgta tttattagcg      60

<210> SEQ ID NO 3
<211> LENGTH: 1300
```

```
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 3
gtacaaataa aactttatct gtacatttcg ttagttaaat tatatttttgt ccatcaaatt    60 gttcctttaa attaaaatct aaaaactaac tttaccgtaa agaaatatgc attcatgtat    120
accaaataaa attttgacaa gagtttaagt tttatattat gattcttaag gaaatcatta    180
tcattataat ttataaaaat aaataaattg ataattatat gctatatcaa tttatgattt    240
gatgagtatg tatgttttaa atgcgagatt ctgccgccgt tcgatatagt tagcagtaga    300
gccctgttct caccctcaca cctgctcagt gtgaacttta aagggactt tgttgacaaa    360 tgttaggatc gtcgtcttct tttgcaataa aaaattttca tctgtttaaa acgtttttat    420
agtaaaatta taaatagaaa atttagttgt aaaatttgaa atataaattt aattagaatg    480
cattcacatt gtaattcttt tacattatta tttattacct aattataaat tatcaacaat    540
aaaatctgac atagtatatg tttagattaa aatttgtaaa tgtaagtttg aattaaaaaa    600
gtatattata aacttgagtt tggtataata ttttttatca tcagactttg gtataatatg    660
agttgatcta aaagtaagtt gaaggatacc aaagggtaat ctaaacatgc atgagaaatg    720
ttggggaata tctttagtgt aaacaaaaag cctataaat tatcatgtca tactatatat    780
gacaaatgtt ggttttgta ataatcattt aaatatgaa caacaggatt ttctttttac    840
cgtcaaaata tgaataaaag ttaaactctt aaattattga tcataggttt gcaattttt    900 tttatagaga ggtttgcaat ttctgagttc tcaataactg atgattaaat gcgcatcgtt    960
tgcatgcatg aaaataaatt taagaggtaa catttgaagt ctcaccttca tgtccggggc   1020
tgccaggaaa gcttagatct ccatgagcat ccacgagctt atccacgagc atccacgagc   1080
ttatccgatt tgagcattga tctccatgag ccatttagtc tcaccttcaa acactgatag   1140
tttaaactga aggcgggaaa cgacaatctg atccccatca agctagcttc tgcaggtcct   1200
gctcgagcgg ccgcagatct tgagccaatc aaagaggagt gatgtagacc taaagcaata   1260
atggagccat gacgtaaggg cttacgccca tacgaaataa                         1300

<210> SEQ ID NO 4
<211> LENGTH: 1947
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 4
atgtactttc attttataat aacgctgcgg acatctacat ttttgaattg aaaaaaaatt    60
ggtaattact ctttctttt ctccatattg accatcatac tcattgctga tccatgtaga   120
tttcccggac tttagctcaa aatgcatgta tttattagcg ttctgtcttt tcgttaattt   180
gttctcatca taatattgtg acaaaaatat agctaggaaa gctttccatg catattttgt   240
aagcaatgaa gtatatagtg gatgcaatgt ctctatatat tcactagtcg agaaaattgc   300
ggacagttct gagattgatt ggcttcatgg ccctacggtg catctattac cattgtcttt   360
gcatttgtca tacaaaaagg tggaccatat tcatgttatg taaaaacaaa caaaatcacg   420
cagtgcacat cttctgcaga atgtgtaggt taaccttatt acacttgatt aagttaagtg   480
```

```
tcatgccatt agtttgagat tgaacttaaa atctttaatc aagatcttag atatggaaaa         540
aattgtaatt ccattaaaga taataagatt tttggataga aattaattat caatttttaca        600 ttaataacat aataatttga agaaaaaaag taagggtcat aatcatacta accagagtaa         660
tttgacacgt gaaggggaca ctatgaaagc aaattacttt tggttcctaa aggttaggca         720
agggaaagaa agaatttgca cttaattagc actattttca aaattattat gtttctttc          780 cttatcttgc ttaaaatttg cttattgtgt tattattatt attattgtta tgcatgatca         840
attattcatc aaagatcgat ctccaacctg ccaggaaatc cgctgatttg tttgcttcca         900
atgtgagaga tccaagatca gaattctgga aggtagtgct gactaccaag gtagcaaaat         960
aatgatattg gggaaggtga aaaatatgta gtactagtac ttctactaca aaatttcaaa        1020
aagggttttg tgattgtgc ataagaatct ttttgcattt gtctgtaagc ttgaaaatta        1080
cacgtggcac aagtcacttg cagccaaaga acctttctgt gaccaattat gttccctgag       1140
ctgaatagtg gttcttattc taatctcatc aatatctaat tacctagtga atatactact       1200
agactattgc agtgttatta atatcttaat gatagactat tgcagcagac agaaattaca       1260
ggtattatta tatactaata tacaattctg cattttccac acttttcccc tgcccatgct       1320
tccatgccac tgaagtctga aaccacattg gcagattttg ctatctagaa attaaataac       1380
aatataagtt tgtatattta tatttcatat tttttagta cattttatt ttgcacactc        1440 tataattcca tgattccttg ttatcggag aatgatgtga tatgcaaacc acgagttaga       1500
accatcaaat caagcaaaga tatggatgga atgcctttaa tggaaagatt aattcaaagg       1560
ggcagaaact ggtaattttt tcttcaactg aatgctatgc agtatgcagc agatctttca       1620
tttacagaat atctgcaaaa ccttgtgttg gagatcttac ctattgaata atgatatagg       1680
taaaataaag tatttaattt caccataact tttaagatga tgttaaaatg atctatgcaa       1740
ttcatgttgg atcgaatatt aaagatgtca catctaatga tactatgata aaaataaagt       1800 ataattctg atcttataag tcaaaataaa tcatgtaaat ataattaat tctcttctta         1860 taaattaatt ttatataatt aagatagatc caatgtgaac tctaagacca tgcatatata       1920
aaaatcatta tcaagtgaat atgcaac                                             1947

<210> SEQ ID NO 5
<211> LENGTH: 3003
<212> TYPE: DNA
<213> ORGANISM: Artificial Sequence
<220> FEATURE:
<223> OTHER INFORMATION: Transgene insert

<400> SEQUENCE: 5
tcaaacactg atagtttaaa ctgaaggcgg gaaacgacaa tctgatcccc atcaagctag          60
cttctgcagg tcctgctcga gcggccgcag atcttgagcc aatcaaagag gagtgatgta         120
gacctaaagc aataatggag ccatgacgta aagggcttacg cccatacgaa ataattaaag        180
gctgatgtga cctgtcggtc tctcagaacc tttactttt atgtttggcg tgtatttta           240 aatttccacg gcaatgacga tgtgacccaa cgagatcttg agccaatcaa agaggagtga         300
tgtagaccta aagcaataat ggagccatga cgtaagggct tacgcccata cgaaataatt         360
aaaggctgat gtgacctgtc ggtctctcag aacctttact ttttatattt ggcgtgtatt         420
tttaaatttc cacggcaatg acgatgtgac ctgtgcatcc gctttgccta taaataagtt        480
ttagtttgta ttgatcgaca cggtcgagaa gacacggcca taagcttgga tcctcgagaa        540
ttctcaacac aacatataca aaacaaacga atctcaagca atcaagcatt ctacttctat        600
```

```
tgcagcaatt taaatcattt cttttaaagc aaaagcaatt ttctgaaaat tttcaccatt    660
tacgaacgat agccatggct tctatgatat cctcttccgc tgtgacaaca gtcagccgtg    720
cctctagggg gcaatccgcc gcaatggctc cattcggcgg cctcaaatcc atgactggat    780
tcccagtgag gaaggtcaac actgacatta cttccattac aagcaatggt ggaagagtaa    840
agtgcatgca ggtgtggcct ccaattggaa agaagaagtt tgagactctt tcctatttgc    900
caccattgac gagagattcc cgggccatgg ccaccttcgt ccgcaatgcc tggtatgtgg    960
cggcgctgcc cgaggaactg tccgaaaagc cgctcggccg gacgattctc gacacaccgc   1020
tcgcgctcta ccgccagccc gacggtgtgg tcgcggcgct gctcgacatc tgtccgcacc   1080
gcttcgcgcc gctgagcgac ggcatcctcg tcaacggcca tctccaatgc cctatcacg   1140 ggctggaatt cgatgcggc gggcagtgcg tccataaccc gcacggcaat ggcgcccgcc   1200
cggcttcgct caacgtccgc tccttcccgg tggtggagcg cgacgcgctg atctggatct   1260
gtcccggcga tccggcgctg gccgatcctg ggcgatccc cgacttcggc tgccgcgtcg   1320
atcccgccta tcggaccgtc ggcggctatg gcatgtcga ctgcaactac aagctgctgg   1380
tcgacaacct gatggacctc ggccacgccc aatatgtcca tcgcgccaac gcccagaccg   1440
acgccttcga ccggctggag cgcgaggtga tcgtcggcga cggtgagata caggcgctga   1500
tgaagattcc cggcggcacg ccgagcgtgc tgatggccaa gttcctgcgc ggcgccaata   1560
cccccgtcga cgcttggaac gacatccgct ggaacaaggt gagcgcgatg ctcaacttca   1620
tcgcggtggc gccggaaggc accccgaagg agcagagcat ccactcgcgc ggtacccata   1680
tcctgacccc cgagacggag gcgagctgcc attatttctt cggctcctcg cgcaatttcg   1740
gcatcgacga tccggagatg gacggcgtgc tgcgcagctg gcaggctcag gcgctggtca   1800
aggaggacaa ggtcgtcgtc gaggcgatcg agcgccgccg cgcctatgtc gaggcgaatg   1860
gcatccgccc ggcgatgctg tcgtgcgacg aagccgcagt ccgtgtcagc cgcgagatcg   1920
agaagcttga gcagctcgaa gccgcctgaa ccggcttatg ctgcacgggc ggggcggggc   1980
ggtttcgatc ggctcgcctg tcccggcgat attctagagc tttcgttcgt atcatcggtt   2040
tcgacaacgt tcgtcaagtt caatgcatca gtttcattgc gcacacacca gaatcctact   2100
gagtttgagt attatggcat tgggaaaact gtttttcttg taccatttgt tgtgcttgta   2160
atttactgtg ttttttattc ggttttcgct atcgaactgt gaaatggaaa tggatggaga   2220
agagttaatg aatgatatgg tccttttgtt cattctcaaa ttaatattat ttgttttttc   2280
tcttatttgt tgtgtgttga atttgaaatt ataagagata tgcaaacatt ttgttttgag   2340
taaaaatgtg tcaaatcgtg gcctctaatg accgaagtta atatgaggag taaaacactt   2400
gtagttgtac cattatgctt attcactagg caacaaatat attttcagac ctagaaaagc   2460
tgcaaatgtt actgaataca agtatgtcct cttgtgtttt agacatttat gaactttcct   2520
ttatgtaatt ttccagaatc cttgtcagat tctaatcatt gctttataat tatagttata   2580
ctcatggatt tgtagttgag tatgaaaata ttttttaatg cattttatga cttgccaatt   2640
gattgacaac atgcatcaat cgcggccgct ctagaactag tggatccccc cctttaaggg   2700
ggctgcagga attcgatatc aagcttggc gcgccaaatc gtgaagtttc tcatctaagc   2760
ccccatttgg acgtgaatgt agacacgtcg aaataaagat ttccgaatta gaataatttg   2820
tttattgctt tcgcctataa atacgacgga tcgtaatttg tcgttttatc aaaatgtact   2880
ttcattttat aataacgctg cggacatcta cattttgaa ttgaaaaaaa attggtaatt   2940
```

```
actctttctt tttctccata ttgaccatca tactcattgc tgatccatgt agatttcccg    3000
gac                                                                 3003

<210> SEQ ID NO 6
<211> LENGTH: 5946
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 6
gtacaaataa aactttatct gtacatttcg ttagttaaat tatattttgt ccatcaaatt      60
gttcctttaa attaaaatct aaaaactaac tttaccgtaa agaaatatgc attcatgtat     120
accaaataaa attttgacaa gagtttaagt tttatattat gattcttaag gaaatcatta     180
tcattataat ttataaaaat aaataaattg ataattatat gctatatcaa tttatgattt     240
gatgagtatg tatgttttaa atgcgagatt ctgccgccgt tcgatatagt tagcagtaga     300
gccctgttct caccctcaca cctgctcagt gtgaacttta aagggacttt tgttgacaaa     360
tgttaggatc gtcgtcttct tttgcaataa aaaattttca tctgtttaaa acgtttttat     420
agtaaaatta taaatagaaa atttagttgt aaaatttgaa atataaattt aattagaatg     480
cattcacatt gtaattcttt tacattatta tttattaccct aattataaat tatcaacaat     540
aaaatctgac atagtatatg tttagattaa aatttgtaaa tgtaagtttg aattaaaaaa     600
gtatattata aacttgagtt tggtataata ttttttatca tcagactttg gtataatatg     660
agttgatcta aaagtaagtt gaaggatacc aaagggtaat ctaaacatgc atgagaaatg     720
ttggggaata tctttagtgt aaacaaaaag ccttataaat tatcatgtca tactatatat     780
gacaaatgtt ggttttttgta ataatcatttt taaatatgaa caacaggatt ttcttttttac    840 cgtcaaaata tgaataaaag ttaaactctt aaattattga tcataggttt gcaattttttt    900 tttatagaga ggtttgcaat ttctgagttc tcaataactg atgattaaat gcgcatcgtt     960
tgcatgcatg aaaataaatt taagaggtaa catttgaagt ctcaccttca tgtccggggc    1020
tgccaggaaa gcttagatct ccatgagcat ccacgagctt atccacgagc atccacgagc    1080
ttatccgatt tgagcattga tctccatgag ccatttagtc tcaccttcaa acactgatag    1140
tttaaactga aggcgggaaa cgacaatctg atccccatca agctagcttc tgcaggtcct    1200
gctcgagcgg ccgcagatct tgagccaatc aaagaggagt gatgtagacc taaagcaata    1260
atggagccat gacgtaaggg cttacgccca tacgaaataa ttaaaggctg atgtgacctg    1320
tcggtctctc agaacctttta ctttttatgt ttggcgtgta ttttttaaatt tccacggcaa    1380 tgacgatgtg acccaacgag atcttgagcc aatcaaagag gagtgatgta gacctaaagc    1440
aataatggag ccatgacgta agggcttacg cccatacgaa ataattaaag gctgatgtga    1500
cctgtcggtc tctcagaacc tttacttttt atatttggcg tgtatttttta aatttccacg    1560 gcaatgacga tgtgacctgt gcatccgctt tgcctataaa taagttttag tttgtattga    1620
tcgacacggt cgagaagaca cggccataag cttggatcct cgagaattct caacacaaca    1680
tatacaaaac aaacgaatct caagcaatca agcattctac ttctattgca gcaatttaaa    1740
tcatttcttt taaagcaaaa gcaatttttct gaaaattttc accatttacg aacgatagcc    1800
atggcttcta tgtatcctc ttccgctgtg acaacagtca gccgtgcctc taggggggcaa    1860 tccgccgcaa tggctccatt cggcggcctc aaatccatga ctggattccc agtgaggaag    1920
```

```
gtcaacactg acattacttc cattacaagc aatggtggaa gagtaaagtg catgcaggtg    1980
tggcctccaa ttggaaagaa gaagtttgag actctttcct atttgccacc attgacgaga    2040
gattcccggg ccatggccac cttcgtccgc aatgcctggt atgtggcggc gctgcccgag    2100
gaactgtccg aaaagccgct cggccggacg attctcgaca caccgctcgc gctctaccgc    2160
cagcccgacg gtgtggtcgc ggcgctgctc gacatctgtc cgcaccgctt cgcgccgctg    2220
agcgacggca tcctcgtcaa cggccatctc caatgcccct atcacgggct ggaattcgat    2280
ggcggcgggc agtgcgtcca taacccgcac ggcaatggcg cccgcccggc ttcgctcaac    2340
gtccgctcct tcccggtggt ggagcgcgac gcgctgatct ggatctgtcc cggcgatccg    2400
gcgctggccg atcctggggc gatccccgac ttcggctgcc gcgtcgatcc cgcctatcgg    2460
accgtcggcg gctatgggca tgtcgactgc aactacaagc tgctggtcga caacctgatg    2520
gacctcggcc acgcccaata tgtccatcgc gccaacgccc agaccgacgc cttcgaccgg    2580
ctggagcgcg aggtgatcgt cggcgacggt gagatacagg cgctgatgaa gattcccggc    2640
ggcacgccga gcgtgctgat ggccaagttc ctgcgcggcg ccaataccccc cgtcgacgct    2700 tggaacgaca tccgctggaa caaggtgagc gcgatgctca acttcatcgc ggtggcgccg    2760
gaaggcaccc cgaaggagca gagcatccac tcgcgcggta cccatatcct gaccccgag    2820 acggaggcga gctgccatta tttcttcggc tcctcgcgca atttcggcat cgacgatccg    2880
gagatggacg gcgtgctgcg cagctggcag gctcaggcgc tggtcaagga ggacaaggtc    2940
gtcgtcgagg cgatcgagcg ccgccgcgcc tatgtcgagg cgaatggcat ccgcccggcg    3000
atgctgtcgt gcgacgaagc cgcagtccgt gtcagccgcg agatcgagaa gcttgagcag    3060
ctcgaagccg cctgaaccgg cttatgctgc acgggcgggg cggggcggtt tcgatcggct    3120
cgcctgtccc ggcgatattc tagagctttc gttcgtatca tcggtttcga caacgttcgt    3180
caagttcaat gcatcagttt cattgcgcac acaccagaat cctactgagt ttgagtatta    3240
tggcattggg aaaactgttt ttcttgtacc atttgttgtg cttgtaattt actgtgtttt    3300
ttattcggtt ttcgctatcg aactgtgaaa tggaaatgga tggagaagag ttaatgaatg    3360
atatggtcct tttgttcatt ctcaaattaa tattatttgt tttttctctt atttgttgtg    3420
tgttgaattt gaaattataa gagatatgca acatttgt tttgagtaaa aatgtgtcaa    3480
atcgtggcct ctaatgaccg aagtaatat gaggagtaaa acacttgtag ttgtaccatt    3540
atgcttattc actaggcaac aaatatattt tcagacctag aaaagctgca aatgttactg    3600
aatacaagta tgtcctcttg tgttttagac atttatgaac tttcctttat gtaattttcc    3660
agaatccttg tcagattcta atcattgctt tataattata gttatactca tggatttgta    3720
gttgagtatg aaaatatttt ttaatgcatt ttatgacttg ccaattgatt gacaacatgc    3780
atcaatcgcg gccgctctag aactagtgga tccccccctt aagggggct gcaggaattc    3840 gatatcaagc tttggcgcgc caaatcgtga agtttctcat ctaagcccc atttggacgt    3900 gaatgtagac acgtcgaaat aaagatttcc gaattagaat aatttgttta ttgctttcgc    3960
ctataaatac gacggatcgt aatttgtcgt tttatcaaaa tgtactttca ttttataata    4020
acgctgcgga catctacatt tttgaattga aaaaaaattg gtaattactc tttcttttc    4080 tccatattga ccatcatact cattgctgat ccatgtagat ttcccggact ttagctcaaa    4140
atgcatgtat ttattagcgt tctgtctttt cgttaatttg ttctcatcat aatattgtga    4200
caaaaatata gctaggaaag cttttccatgc atattttgta agcaatgaag tatatagtgg    4260
atgcaatgtc tctatatatt cactagtcga gaaaattgcg gacagttctg agattgattg    4320
```

```
gcttcatggc cctacggtgc atctattacc attgtctttg catttgtcat acaaaaaggt    4380
ggaccatatt catgttatgt aaaaacaaac aaaatcacgc agtgcacatc ttctgcagaa    4440
tgtgtaggtt aaccttatta cacttgatta agttaagtgt catgccatta gtttgagatt    4500
gaacttaaaa tctttaatca agatcttaga tatggaaaaa attgtaattc cattaaagat    4560
aataagattt ttggatagaa attaattatc aatttacat taataacata ataatttgaa    4620
gaaaaaaagt aagggtcata atcatactaa ccagagtaat ttgacacgtg aaggggacac    4680
tatgaaagca aattactttt ggttcctaaa ggttaggcaa gggaaagaaa gaatttgcac    4740
ttaattagca ctattttcaa aattattatg tttcttttcc ttatcttgct aaaaatttgc    4800
ttattgtgtt attattatta ttattgttat gcatgatcaa ttattcatca agatcgatc     4860 tccaacctgc caggaaatcc gctgatttgt ttgcttccaa tgtgagagat ccaagatcag    4920
aattctggaa ggtagtgctg actaccaagg tagcaaaata atgatattgg ggaaggtgaa    4980
aaatatgtag tactagtact tctactacaa aatttcaaaa agggttttgt gatttgtgca    5040
taagaatctt tttgcatttg tctgtaagct tgaaaattac acgtggcaca agtcacttgc    5100
agccaaagaa cctttctgtg accaattatg ttccctgagc tgaatagtgg ttcttattct    5160
aatctcatca atatctaatt acctagtgaa tatactacta gactattgca gtgttattaa    5220
tatcttaatg atagactatt gcagcagaca gaaattacag gtattattat atactaatat    5280
acaattctgc atttcccaca cttttcccct gcccatgctt ccatgccact gaagtctgaa    5340
accacattgg cagattttgc tatctagaaa ttaaataaca atataagttt gtatatttat    5400
atttcatatt ttttagtac attttttattt tgcacactct ataattccat gattccttga    5460
ttatcggaga atgatgtgat atgcaaacca cgagttagaa ccatcaaatc aagcaaagat    5520
atggatggaa tgcctttaat ggaaagatta attcaaaggg gcagaaactg gtaatttttt    5580
cttcaactga atgctatgca gtatgcagca gatctttcat ttacagaata tctgcaaaac    5640
cttgtgttgg agatcttacc tattgaataa tgatataggt aaaataaagt atttaatttc    5700
accataactt ttaagatgat gttaaaatga tctatgcaat tcatgttgga tcgaatatta    5760
aagatgtcac atcaatgat actatgataa aaataaagta taattctga tcttataagt     5820 caaaataaat catgtaaata taaattaatt ctcttcttat aaattaattt tatataatta    5880
agatagatcc aatgtgaact ctaagaccat gcatatataa aaatcattat caagtgaata    5940
tgcaac                                                              5946
```

```
<210> SEQ ID NO 7
<211> LENGTH: 100
<212> TYPE: DNA
<213> ORGANISM: Artificial Sequence
<220> FEATURE:
<223> OTHER INFORMATION: Chimeric DNA molecule of soybean genomic DNA
      and transgene DNA

<400> SEQUENCE: 7
gagcttatcc gatttgagca ttgatctcca tgagccattt agtctcacct tcaaacactg    60
atagtttaaa ctgaaggcgg gaaacgacaa tctgatcccc                          100

<210> SEQ ID NO 8
<211> LENGTH: 100
<212> TYPE: DNA
<213> ORGANISM: Artificial Sequence
<220> FEATURE:
<223> OTHER INFORMATION: Chimeric DNA molecule of soybean genomic DNA
``` and transgene DNA

<400> SEQUENCE: 8
ctccatattg accatcatac tcattgctga tccatgtaga tttcccggac tttagctcaa    60
aatgcatgta tttattagcg ttctgtcttt tcgttaattt    100

<210> SEQ ID NO 9
<211> LENGTH: 27
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 9
ttttctccat attgaccatc atactca    27

<210> SEQ ID NO 10
<211> LENGTH: 28
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 10
agacagaacg ctaataaata catgcatt    28

<210> SEQ ID NO 11
<211> LENGTH: 18
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
ttcccggact ttagctca    18

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
gatttcccgg actttagctc aa    22

<210> SEQ ID NO 13
<211> LENGTH: 30
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 13
tcacaatatt atgatgagaa caaattaacg    30

<210> SEQ ID NO 14
<211> LENGTH: 25
<212> TYPE: DNA
<213> ORGANISM: Artificial Sequence
<220> FEATURE:

```
<223> OTHER INFORMATION: Chemically Synthesized Oligonucleotide PCR
      Primer

<400> SEQUENCE: 14
gcccctaatg gatttttaac ttttc                                            25

<210> SEQ ID NO 15
<211> LENGTH: 22
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 15
atgcatgtat ttattagcgt tc                                               22

<210> SEQ ID NO 16
<211> LENGTH: 18
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 16
acatgtgtga ctacttct                                                    18
```